US010533232B2

(12) United States Patent
Chen et al.

(10) Patent No.: US 10,533,232 B2
(45) Date of Patent: Jan. 14, 2020

(54) PARASITIC PHYTOPHTHORA-DERIVED OMEGA-3 FATTY ACID DESATURASE FOR SYNTHESIZING POLYUNSATURATED FATTY ACIDS, CARRIER CONTAINING FATTY ACID DESATURASE, RECOMBINANT MICROORGANISMS, AND APPLICATION THEREOF

(71) Applicant: JIANGNAN UNIVERSITY, Wuxi (CN)

(72) Inventors: Haiqin Chen, Wuxi (CN); Yongquan Chen, Wuxi (CN); Wei Chen, Wuxi (CN); Tiantian Mei, Wuxi (CN); Zhennan Gu, Wuxi (CN); Hao Zhang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 22 days.

(21) Appl. No.: 16/060,417

(22) PCT Filed: Dec. 8, 2016

(86) PCT No.: PCT/CN2016/108983

§ 371 (c)(1),
(2) Date: Jun. 7, 2018

(87) PCT Pub. No.: WO2017/097218

PCT Pub. Date: Jun. 15, 2017

(65) Prior Publication Data

US 2019/0233908 A1 Aug. 1, 2019

(30) Foreign Application Priority Data

Dec. 9, 2015 (CN) .......................... 2015 1 0902579
Mar. 28, 2016 (CN) .......................... 2016 1 0184669

(51) Int. Cl.
*C12R 1/645* (2006.01)
*C12N 1/14* (2006.01)
*C12N 9/02* (2006.01)
*C12N 15/82* (2006.01)

(52) U.S. Cl.
CPC ................ *C12R 1/645* (2013.01); *C12N 1/14* (2013.01); *C12N 9/0071* (2013.01); *C12N 15/8201* (2013.01); *C12Y 114/19006* (2013.01)

(58) Field of Classification Search
None
See application file for complete search history.

*Primary Examiner* — Kagnew H Gebreyesus

(74) *Attorney, Agent, or Firm* — CBM Patent Consulting, LLC

(57) ABSTRACT

It relates to ω-3 fatty acid desaturase for the synthesis of pufas from *Phytophthora parasitica*, a plasmid containing the same, a recombinant microorganism containing the plasmid and its application. The invention also provides the use of the above ω-3 fatty acid desaturase in the biosynthesis of PUFAs, especially to catalyze $C20:4^{\Delta5,8,11,14}$ to $C20:5^{\Delta5,8,11,14,17}$ at normal temperature, with catalytic efficiency 65%. The recombinant strain reached 31.5% of the total fatty acid, and the conversion rate to AA was up to 77.6%.

10 Claims, 5 Drawing Sheets

Specification includes a Sequence Listing.

SEQUENCE LISTING

```
<160> NUMBER OF SEQ ID NOS: 39

<210> SEQ ID NO 1
<211> LENGTH: 1086
<212> TYPE: DNA
<213> ORGANISM: Phytophthora parasitica

<400> SEQUENCE: 1

atggcgacga agcaggcgta tgtgttcccg accctgacgg agatcaagcg gtcgctgccc      60

agcgagtgct tcgaggcctc agtgcctctg tcgctctact acactgtgcg ttgtctcgtg     120

atcgccgtgg ctcttgcgtt cggtctcaac tacgctcgcg gactccccgt ggtcgagaac     180

ttgtgggctc tggacgccgc tctctgcacg ggctacattt tgctgcaggg catcgtgttt     240

tggggcttct tcacggtggg ccacgacgct ggccacggcg ccttctcgcg ttaccacttg     300
```

```
ctcaacttcg tggtgggcac tttcatccac tcgctcatcc tcacgccctt cgagtcgtgg    360

aagctcacgc accgtcacca ccacaagaac acgggcaaca tcgaccgtga tgagatcttt    420

tacccgcaac gcaaggccga tgaccacccg ttgtctcgca atctcatcct ggcgctcggt    480

gccgcgtggt tcgcctactt gatcgagggt ttcccgcctc gtaaggtcaa ccacttcaac    540

ccgttcgagc ctctgttcgt gcgccaggtg tcggctgtgg tgatctctct cctcgcccac    600

ttcttcgtgg cgggactctc catctatctg agcctccagt tgggcctcaa gactatggca    660

atctactact acgggcctat cttcgtgttc ggtagcatgc tggtgatcac caccttcctg    720

caccacaacg acgaggaaac tccgtggtac gcagactccg agtggacgta cgtcaaggga    780

aacctctcgt ccgtggaccg atcctacgga gcgcttattg acaacctgag ccacaacatc    840

ggcacgcacc agatccacca cctcttccct atcatcccgc actacaaact caagaaagcc    900

actgcggcct tccaccaggc tttccccgag ctcgtgcgta agagcgacga gccaatcatc    960

acggctttct tccgagtcgg acgtctctac gccaactacg gcgtcgtgga cccggaggcc   1020

aagctcttca cgctcaagga agccaaggcg gcgaacgagg cggcggtgaa gaccaagtct   1080

acctaa                                                              1086
```

<210> SEQ ID NO 2
<211> LENGTH: 361
<212> TYPE: PRT
<213> ORGANISM: Phytophthora parasitica

<400> SEQUENCE: 2

```
Met Ala Thr Lys Gln Ala Tyr Val Phe Pro Thr Leu Thr Glu Ile Lys
1               5                   10                  15

Arg Ser Leu Pro Ser Glu Cys Phe Glu Ala Ser Val Pro Leu Ser Leu
            20                  25                  30

Tyr Tyr Thr Val Arg Cys Leu Val Ile Ala Val Ala Leu Ala Phe Gly
        35                  40                  45

Leu Asn Tyr Ala Arg Gly Leu Pro Val Val Glu Asn Leu Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Ile His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Ile Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Phe Ala Tyr Leu Ile Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Ile Phe Val Phe Gly Ser Met Leu Val Ile Thr Thr Phe Leu
```

```
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Thr Ala Phe Phe Arg Val Gly Arg Leu Tyr Ala Asn Tyr Gly Val Val
                325                 330                 335

Asp Pro Glu Ala Lys Leu Phe Thr Leu Lys Glu Ala Lys Ala Ala Asn
            340                 345                 350

Glu Ala Ala Val Lys Thr Lys Ser Thr
        355                 360


<210> SEQ ID NO 3
<211> LENGTH: 1086
<212> TYPE: DNA
<213> ORGANISM: Phytophthora parasitica

<400> SEQUENCE: 3

atggcaacca agcaagccta tgtattccct actttgactg aaattaagag aagtttacca     60

tctgaatgtt ttgaagcatc cgttccattg tcattatact acactgttag atgtttggta    120

attgcagttg ccttagcttt tggtttgaat tacgcaagag gtttaccagt tgtcgaaaac    180

ttatgggcct tggatgctgc attgtgcaca ggttacatat tgttacaagg tatcgtattt    240

tggggtttct ttaccgttgg tcacgatgca ggtcatggtg ccttctccag ataccacttg    300

ttgaacttcg tagttggtac attcatccat tccttgatct taacccottt tgaaagttgg    360

aaattgactc atagacatca ccataagaat actggtaaca tcgatagaga cgaaattttc    420

tacccacaaa gaaaagctga tgaccatcct ttgtcaagaa atttgatctt agccttgggt    480

gccgcttggt ttgcttattt gattgaaggt ttcccaccta gaaaggttaa ccatttcaac    540

ccattcgaac ctttgtttgt cagacaagta tctgctgttg taatatcatt gttagctcat    600

ttctttgttg caggtttgtc catatactta agtttgcaat tgggtttgaa gacaatggct    660

atctactact acggtccaat cttcgttttc ggttccatgt tggtcatcac tacatttttg    720

caccataacg atgaagaaac cccttggtac gcagacagtg aatggactta tgtcaagggt    780

aacttatctt cagtagatag atcctatggt gctttgattg acaatttgtc acacaacata    840

ggtactcatc aaatccacca tttgttccca ataatccctc actacaaatt gaaaaaggca    900

acagcagcct ttcatcaagc cttcccagaa ttagttagaa agtctgatga acctatcatt    960

accgcctttt tcagagtcgg tagattgtac gctaattatg gtgttgttga tccagaagct   1020

aaattgttca cattgaagga agcaaaggct gcaaacgaag ccgctgttaa aaccaagtca   1080

acttaa                                                              1086


<210> SEQ ID NO 4
<211> LENGTH: 361
<212> TYPE: PRT
<213> ORGANISM: Phytophthora parasitica

<400> SEQUENCE: 4
```

```
Met Ala Thr Lys Gln Ala Tyr Val Phe Pro Thr Leu Thr Glu Ile Lys
1               5                   10                  15

Arg Ser Leu Pro Ser Glu Cys Phe Glu Ala Ser Val Pro Leu Ser Leu
            20                  25                  30

Tyr Tyr Thr Val Arg Cys Leu Val Ile Ala Val Ala Leu Ala Phe Gly
        35                  40                  45

Leu Asn Tyr Ala Arg Gly Leu Pro Val Val Glu Asn Leu Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Ile His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Ile Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Phe Ala Tyr Leu Ile Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Ile Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Thr Ala Phe Phe Arg Val Gly Arg Leu Tyr Ala Asn Tyr Gly Val Val
                325                 330                 335

Asp Pro Glu Ala Lys Leu Phe Thr Leu Lys Glu Ala Lys Ala Ala Asn
            340                 345                 350

Glu Ala Ala Val Lys Thr Lys Ser Thr
        355                 360
```

<210> SEQ ID NO 5
<211> LENGTH: 1086
<212> TYPE: DNA
<213> ORGANISM: Phytophthora parasitica

<400> SEQUENCE: 5

```
atggctacca agcaggccta cgtcttcccc accctcaccg agatcaagcg ttcgttgccc     60
```

```
tccgagtgct ttgaggcctc ggtccctctc tccttgtact acaccgttcg ctgcttggtc    120

atcgccgttg ctctcgcctt cggattgaac tacgctcgtg gcttgcctgt cgttgagaac    180

ctgtgggctc tcgacgctgc tctgtgcacc ggttacatcc tcttgcaggg aattgtcttc    240

tggggcttct ttaccgttgg tcacgatgct ggccacggtg ccttttcgcg ctaccacctg    300

ctcaacttcg tcgttggaac ctttatccac tcgctgattc tcaccccttt cgagtcctgg    360

aagctcaccc accgtcacca ccacaagaac accggcaaca tcgaccgcga tgagatcttc    420

taccctcagc gtaaggccga cgatcaccct ctctcccgca acttgatcct ggctctcgga    480

gccgcttggt tcgcctactt gattgagggc tttccccctc gcaaggtcaa ccacttcaac    540

ccctttgagc ctttgttcgt ccgtcaggtt tcggccgtcg ttatctcctt gctggctcac    600

ttctttgtcg ccggtctgtc gatctacttg tccctgcagc tcggattgaa gaccatggcc    660

atctactact acggtcccat tttcgtcttt ggatcgatgt tggttatcac caccttcctg    720

caccacaacg acgaggagac cccttggtac gccgattccg agtggaccta cgtcaagggc    780

aacctctcgt ccgttgaccg ttcgtacggt gccctgatcg ataacctctc ccacaacatc    840

ggcacccacc agattcacca cctgttcccc atcattcctc actacaagct caagaaggct    900

accgccgctt tccaccaggc ctttcccgag ctggtccgca agtcggacga gcctatcatt    960

accgctttct ttcgcgtcgg ccgtctctac gccaactacg gtgtcgttga tcccgaggct   1020

aagttgttca ccctgaagga agccaaggcc gctaacgagg ccgctgtcaa gaccaagtcc   1080

acctaa                                                               1086
```

```
<210> SEQ ID NO 6
<211> LENGTH: 361
<212> TYPE: PRT
<213> ORGANISM: Phytophthora parasitica

<400> SEQUENCE: 6

Met Ala Thr Lys Gln Ala Tyr Val Phe Pro Thr Leu Thr Glu Ile Lys
1               5                   10                  15

Arg Ser Leu Pro Ser Glu Cys Phe Glu Ala Ser Val Pro Leu Ser Leu
            20                  25                  30

Tyr Tyr Thr Val Arg Cys Leu Val Ile Ala Val Ala Leu Ala Phe Gly
        35                  40                  45

Leu Asn Tyr Ala Arg Gly Leu Pro Val Val Glu Asn Leu Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Ile His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Ile Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Phe Ala Tyr Leu Ile Glu Gly Phe Pro Pro Arg Lys Val
                165                 170                 175

Asn His Phe Asn Pro Phe Glu Pro Leu Phe Val Arg Gln Val Ser Ala
```

```
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Ile Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Thr Ala Phe Phe Arg Val Gly Arg Leu Tyr Ala Asn Tyr Gly Val Val
                325                 330                 335

Asp Pro Glu Ala Lys Leu Phe Thr Leu Lys Glu Ala Lys Ala Ala Asn
            340                 345                 350

Glu Ala Ala Val Lys Thr Lys Ser Thr
        355                 360


<210> SEQ ID NO 7
<211> LENGTH: 1095
<212> TYPE: DNA
<213> ORGANISM: Aphanomyces invadans

<400> SEQUENCE: 7

atgccgtcgc ccaaggcaac ctccggagca gcggctcctg cggccgatgt cgagttcccg      60

accttgacgg aactcaagca ttcgattccg aattcgtgct ttgagtcgga tgctaccatt     120

tcactctact acgtttttcg atcagtagca ttgactgctg cgttgatgac gggactcact     180

catgcccgcg ctgccgtcgc cgactggatg gtgctagacc tcctgatatc ccttgcgtac     240

gtgtacgtgc aaggcgtggt gttctggggc gtgttcacca ttggccacga ctgcggacac     300

agctcgtttt ctcgatacca caacctcaac tttattgtgg gctgcatcat gcactctgcg     360

atcttgactc cattcgagag ctggcgcatc acccatcgcc accaccacaa aaacacgggc     420

aacgtggaca aggacgaagt gttttacccg caacgcgaaa aggacgagta ccccatgacc     480

cgcaagattg tgtacacact cggtctgtcc tggttcatct acctcaagca aggctacgtg     540

ccgcgcacca tgaaccactt caacccttgg gacccgctcc tcgtccgtcg gacggccgct     600

gtgatcgtgt cgctcgggtt ctggctgtcg gggtcgcga tcgttgggta cctgaccctc     660

accttgggca tcaaaacgat ggctctgtac tactttgcgc ctctgtttgt gtttgcctcg     720

tttctggtcg tcacgacctt tttgcaccac aatgatgaaa acacgccttg gtacggcgac     780

tcgtcgtgga cgtacgtcaa gggcaacctg tcgagcgtcg accgcagcta cggctggctc     840

gtcgacgagc tgagccacaa cattgggacg catcaagtcc accacttgtt cccgatcatc     900

ccgcactaca agctcaatga cgcaacaagc cactttcgca aggccttccc gcacctcgtc     960

cgtgtcagca acgaaccgat cgtgcccgcg ttcttcaaga cgctcgattt gttcgtacac    1020

tatggcatcg tgccggacaa cgcggaaatc tttacgctgc gcgaacgtgc taactcggtg    1080
```

```
aagaagacgc tttag                                                   1095


<210> SEQ ID NO 8
<211> LENGTH: 364
<212> TYPE: PRT
<213> ORGANISM: Aphanomyces invadans

<400> SEQUENCE: 8

Met Pro Ser Pro Lys Ala Thr Ser Gly Ala Ala Ala Pro Ala Ala Asp
1               5                   10                  15

Val Glu Phe Pro Thr Leu Thr Glu Leu Lys His Ser Ile Pro Asn Ser
            20                  25                  30

Cys Phe Glu Ser Asp Ala Thr Ile Ser Leu Tyr Tyr Val Phe Arg Ser
        35                  40                  45

Val Ala Leu Thr Ala Ala Leu Met Thr Gly Leu Thr His Ala Arg Ala
    50                  55                  60

Ala Val Ala Asp Trp Met Val Leu Asp Leu Leu Ile Ser Leu Ala Tyr
65                  70                  75                  80

Val Tyr Val Gln Gly Val Val Phe Trp Gly Val Phe Thr Ile Gly His
                85                  90                  95

Asp Cys Gly His Ser Ser Phe Ser Arg Tyr His Asn Leu Asn Phe Ile
            100                 105                 110

Val Gly Cys Ile Met His Ser Ala Ile Leu Thr Pro Phe Glu Ser Trp
        115                 120                 125

Arg Ile Thr His Arg His His Lys Asn Thr Gly Asn Val Asp Lys
    130                 135                 140

Asp Glu Val Phe Tyr Pro Gln Arg Glu Lys Asp Glu Tyr Pro Met Thr
145                 150                 155                 160

Arg Lys Ile Val Tyr Thr Leu Gly Leu Ser Trp Phe Ile Tyr Leu Lys
                165                 170                 175

Gln Gly Tyr Val Pro Arg Thr Met Asn His Phe Asn Pro Trp Asp Pro
            180                 185                 190

Leu Leu Val Arg Arg Thr Ala Ala Val Ile Val Ser Leu Gly Phe Trp
        195                 200                 205

Leu Ser Gly Val Ala Ile Val Gly Tyr Leu Thr Leu Thr Leu Gly Ile
    210                 215                 220

Lys Thr Met Ala Leu Tyr Tyr Phe Ala Pro Leu Phe Val Phe Ala Ser
225                 230                 235                 240

Phe Leu Val Val Thr Thr Phe Leu His His Asn Asp Glu Asn Thr Pro
                245                 250                 255

Trp Tyr Gly Asp Ser Ser Trp Thr Tyr Val Lys Gly Asn Leu Ser Ser
            260                 265                 270

Val Asp Arg Ser Tyr Gly Trp Leu Val Asp Glu Leu Ser His Asn Ile
        275                 280                 285

Gly Thr His Gln Val His His Leu Phe Pro Ile Ile Pro His Tyr Lys
    290                 295                 300

Leu Asn Asp Ala Thr Ser His Phe Arg Lys Ala Phe Pro His Leu Val
305                 310                 315                 320

Arg Val Ser Asn Glu Pro Ile Val Pro Ala Phe Phe Lys Thr Leu Asp
                325                 330                 335

Leu Phe Val His Tyr Gly Ile Val Pro Asp Asn Ala Glu Ile Phe Thr
            340                 345                 350

Leu Arg Glu Arg Ala Asn Ser Val Lys Lys Thr Leu
        355                 360
```

<210> SEQ ID NO 9
<211> LENGTH: 1095
<212> TYPE: DNA
<213> ORGANISM: Aphanomyces invadans

<400> SEQUENCE: 9

```
atgccatccc ctaaagccac atccggtgcc gccgccccag cagccgacgt tgaatttcct     60

accttgactg aattaaaaca ctccatacca aattcctgtt ttgaaagtga tgccactatt    120

tccttgtatt acgttttcag aagtgtcgct ttaacagctg cattgatgac aggtttaacc    180

catgctagag ccgctgtagc agattggatg gttttggact tgttaatttc cttagcttat    240

gtctacgtac aaggtgttgt cttttggggt gttttcacaa taggtcacga ttgtggtcat    300

tcttcatttt caagatacca caacttgaac ttcatcgttg gttgcattat gcattctgca    360

attttaaccc catttgaatc atggagaatc actcatagac atcaccataa gaacactggt    420

aacgtcgata aggacgaagt attctatcca caaagagaaa aggatgaata ccctatgact    480

agaaagatcg tttatacatt gggtttgtct tggttcatat acttgaaaca aggttacgtt    540

cctagaacca tgaatcattt caacccttgg gacccattgt tagtcagaag aactgctgct    600

gttattgtct ctttgggttt ttggttatca ggtgtcgcaa tagtaggtta tttgacctta    660

actttgggta tcaaaacaat ggccttgtac tacttcgctc cattgttcgt tttcgcttca    720

tttttggtag ttactacatt cttacaccat aacgatgaaa acaccccttg gtatggtgac    780

tccagttgga cttacgtaaa gggtaatttg tcttcagttg atagatccta cggttggttg    840

gttgatgaat taagtcacaa cattggtaca catcaagtac accatttgtt cccaataatc    900

cctcactaca aattgaatga tgcaacctct cactttagaa aggccttccc acatttagta    960

agagtttcaa acgaaccaat tgttcctgct ttctttaaga ctttagattt gttcgttcat   1020

tacggtatag tccctgacaa tgctgaaatc ttcacattga gagaaagagc aaactcagtt   1080

aaaaagacct tataa                                                    1095
```

<210> SEQ ID NO 10
<211> LENGTH: 364
<212> TYPE: PRT
<213> ORGANISM: Aphanomyces invadans

<400> SEQUENCE: 10

```
Met Pro Ser Pro Lys Ala Thr Ser Gly Ala Ala Ala Pro Ala Ala Asp
1               5                   10                  15

Val Glu Phe Pro Thr Leu Thr Glu Leu Lys His Ser Ile Pro Asn Ser
            20                  25                  30

Cys Phe Glu Ser Asp Ala Thr Ile Ser Leu Tyr Tyr Val Phe Arg Ser
        35                  40                  45

Val Ala Leu Thr Ala Ala Leu Met Thr Gly Leu Thr His Ala Arg Ala
    50                  55                  60

Ala Val Ala Asp Trp Met Val Leu Asp Leu Leu Ile Ser Leu Ala Tyr
65                  70                  75                  80

Val Tyr Val Gln Gly Val Val Phe Trp Gly Val Phe Thr Ile Gly His
                85                  90                  95

Asp Cys Gly His Ser Ser Phe Ser Arg Tyr His Asn Leu Asn Phe Ile
            100                 105                 110

Val Gly Cys Ile Met His Ser Ala Ile Leu Thr Pro Phe Glu Ser Trp
        115                 120                 125

Arg Ile Thr His Arg His His His Lys Asn Thr Gly Asn Val Asp Lys
```

```
    130                 135                 140

Asp Glu Val Phe Tyr Pro Gln Arg Glu Lys Asp Glu Tyr Pro Met Thr
145                 150                 155                 160

Arg Lys Ile Val Tyr Thr Leu Gly Leu Ser Trp Phe Ile Tyr Leu Lys
                165                 170                 175

Gln Gly Tyr Val Pro Arg Thr Met Asn His Phe Asn Pro Trp Asp Pro
            180                 185                 190

Leu Leu Val Arg Arg Thr Ala Ala Val Ile Val Ser Leu Gly Phe Trp
        195                 200                 205

Leu Ser Gly Val Ala Ile Val Gly Tyr Leu Thr Leu Thr Leu Gly Ile
    210                 215                 220

Lys Thr Met Ala Leu Tyr Tyr Phe Ala Pro Leu Phe Val Phe Ala Ser
225                 230                 235                 240

Phe Leu Val Val Thr Thr Phe Leu His His Asn Asp Glu Asn Thr Pro
                245                 250                 255

Trp Tyr Gly Asp Ser Ser Trp Thr Tyr Val Lys Gly Asn Leu Ser Ser
            260                 265                 270

Val Asp Arg Ser Tyr Gly Trp Leu Val Asp Glu Leu Ser His Asn Ile
        275                 280                 285

Gly Thr His Gln Val His His Leu Phe Pro Ile Ile Pro His Tyr Lys
    290                 295                 300

Leu Asn Asp Ala Thr Ser His Phe Arg Lys Ala Phe Pro His Leu Val
305                 310                 315                 320

Arg Val Ser Asn Glu Pro Ile Val Pro Ala Phe Phe Lys Thr Leu Asp
                325                 330                 335

Leu Phe Val His Tyr Gly Ile Val Pro Asp Asn Ala Glu Ile Phe Thr
            340                 345                 350

Leu Arg Glu Arg Ala Asn Ser Val Lys Lys Thr Leu
        355                 360
```

<210> SEQ ID NO 11
<211> LENGTH: 29
<212> TYPE: DNA
<213> ORGANISM: Artificial Sequence
<220> FEATURE:
<223> OTHER INFORMATION: It is synthesized

<400> SEQUENCE: 11
ctaattgaat tcatggcaac caagcaagc 29

<210> SEQ ID NO 12
<211> LENGTH: 36
<212> TYPE: DNA
<213> ORGANISM: Artificial Sequence
<220> FEATURE:
<223> OTHER INFORMATION: It is sythesized.

<400> SEQUENCE: 12
cgattctcga gttaagttga cttggtttta acagcg 36

<210> SEQ ID NO 13
<211> LENGTH: 32
<212> TYPE: DNA
<213> ORGANISM: Artificial Sequence
<220> FEATURE:
<223> OTHER INFORMATION: It is synthesized.

<400> SEQUENCE: 13
acaatggaat tcatgccatc ccctaaagcc ac 32

<210> SEQ ID NO 14
<211> LENGTH: 42
<212> TYPE: DNA
<213> ORGANISM: Artificial Sequence
<220> FEATURE:
<223> OTHER INFORMATION: It is synthesized.

<400> SEQUENCE: 14
cctgatctcg agttataagg tctttttaac tgagtttgct ct 42

<210> SEQ ID NO 15
<211> LENGTH: 31
<212> TYPE: DNA
<213> ORGANISM: Artificial Sequence
<220> FEATURE:
<223> OTHER INFORMATION: It is synthesized.

<400> SEQUENCE: 15
catgtagaat tcatggcttc gtccaccgtt g 31

<210> SEQ ID NO 16
<211> LENGTH: 35
<212> TYPE: DNA
<213> ORGANISM: Artificial Sequence
<220> FEATURE:
<223> OTHER INFORMATION: It is synthesized.

<400> SEQUENCE: 16
ttacgactcg agttagttag ccttggtctt ggcag 35

<210> SEQ ID NO 17
<211> LENGTH: 20
<212> TYPE: DNA
<213> ORGANISM: Artificial Sequence
<220> FEATURE:
<223> OTHER INFORMATION: It is synthesized.

<400> SEQUENCE: 17
taatacgact cactataggg 20

<210> SEQ ID NO 18
<211> LENGTH: 18
<212> TYPE: DNA
<213> ORGANISM: Artificial Sequence
<220> FEATURE:
<223> OTHER INFORMATION: It is synthesized.

<400> SEQUENCE: 18
tcggttagag cggatgtg 18

<210> SEQ ID NO 19
<211> LENGTH: 22
<212> TYPE: DNA
<213> ORGANISM: Artificial Sequence
<220> FEATURE:
<223> OTHER INFORMATION: It is synthesized.

<400> SEQUENCE: 19
ggcaaccaag caagcctatg ta 22

<210> SEQ ID NO 20
<211> LENGTH: 25
<212> TYPE: DNA
<213> ORGANISM: Artificial Sequence
<220> FEATURE:

<223> OTHER INFORMATION: It is synthesized.

<400> SEQUENCE: 20
tactacttcg ctccattgtt cgttt 25

<210> SEQ ID NO 21
<211> LENGTH: 25
<212> TYPE: DNA
<213> ORGANISM: Artificial Sequence
<220> FEATURE:
<223> OTHER INFORMATION: It is synthesized.

<400> SEQUENCE: 21
caaccgtagg atctatcaac tgaag 25

<210> SEQ ID NO 22
<211> LENGTH: 18
<212> TYPE: DNA
<213> ORGANISM: Artificial Sequence
<220> FEATURE:
<223> OTHER INFORMATION: It is synthesized.

<400> SEQUENCE: 22
cttcgtccac cgttgctg 18

<210> SEQ ID NO 23
<211> LENGTH: 17
<212> TYPE: DNA
<213> ORGANISM: Artificial Sequence
<220> FEATURE:
<223> OTHER INFORMATION: It is synthesized.

<400> SEQUENCE: 23
agccagcgat tccgaga 17

<210> SEQ ID NO 24
<211> LENGTH: 26
<212> TYPE: DNA
<213> ORGANISM: Artificial Sequence
<220> FEATURE:
<223> OTHER INFORMATION: It is synthesized.

<400> SEQUENCE: 24
aatcatcaaa gagtccgaag acattg 26

<210> SEQ ID NO 25
<211> LENGTH: 25
<212> TYPE: DNA
<213> ORGANISM: Artificial Sequence
<220> FEATURE:
<223> OTHER INFORMATION: It is synthesized.

<400> SEQUENCE: 25
cctttactac atggtataac tgtgg 25

<210> SEQ ID NO 26
<211> LENGTH: 23
<212> TYPE: DNA
<213> ORGANISM: Artificial Sequence
<220> FEATURE:
<223> OTHER INFORMATION: It is synthesized.

<400> SEQUENCE: 26
cacacacaaa cctctctccc act 23

<210> SEQ ID NO 27
<211> LENGTH: 26
<212> TYPE: DNA
<213> ORGANISM: Artificial Sequence
<220> FEATURE:
<223> OTHER INFORMATION: It is synthesized.

<400> SEQUENCE: 27
caaatgaacg tatcttatcg agatcc 26

<210> SEQ ID NO 28
<211> LENGTH: 18
<212> TYPE: DNA
<213> ORGANISM: Artificial Sequence
<220> FEATURE:
<223> OTHER INFORMATION: It is synthesized.

<400> SEQUENCE: 28
tcttccccac cctcaccg 18

<210> SEQ ID NO 29
<211> LENGTH: 20
<212> TYPE: DNA
<213> ORGANISM: Artificial Sequence
<220> FEATURE:
<223> OTHER INFORMATION: It is synthesized.

<400> SEQUENCE: 29
caagccacga gcgtagttca 20

<210> SEQ ID NO 30
<211> LENGTH: 24
<212> TYPE: DNA
<213> ORGANISM: Artificial Sequence
<220> FEATURE:
<223> OTHER INFORMATION: It is synthesized.

<400> SEQUENCE: 30
cgtactaccg attgaatggc ttag 24

<210> SEQ ID NO 31
<211> LENGTH: 23
<212> TYPE: DNA
<213> ORGANISM: Artificial Sequence
<220> FEATURE:
<223> OTHER INFORMATION: It is synthesized.

<400> SEQUENCE: 31
cctacggaaa ccttgttacg act 23

<210> SEQ ID NO 32
<211> LENGTH: 1086
<212> TYPE: DNA
<213> ORGANISM: Phytophthora parasitica

<400> SEQUENCE: 32
atggctacca agcaggccta cgtcttcccc accctcaccg agatcaagcg ttcgttgccc 60
tccgagtgct ttgaggcctc ggtccctctc tccttgtact acaccgttcg ctgcttggtc 120
atcgccgttg ctctcgcctt cggattgaac tacgctcgtg gcttgcctgt cgttgagaac 180
ctgtgggctc tcgacgctgc tctgtgcacc ggttacatcc tcttgcaggg aattgtcttc 240
tggggcttct ttaccgttgg tcacgatgct ggccacggtg ccttttcgcg ctaccacctg 300
ctcaacttcg tcgttggaac ctttatccac tcgctgattc tcacccccttt cgagtcctgg 360

```
aagctcaccc accgtcacca ccacaagaac accggcaaca tcgaccgcga tgagatcttc    420

taccctcagc gtaaggccga cgatcaccct ctctcccgca acttgatcct ggctctcgga    480

gccgcttggt tcgcctactt gattgagggc tttccccctc gcaaggtcaa ccacttcaac    540

ccctttgagc ctttgttcgt ccgtcaggtt tcggccgtcg ttatctcctt gctggctcac    600

ttctttgtcg ccggtctgtc gatctacttg tccctgcagc tcggattgaa gaccatggcc    660

atctactact acggtcccat tttcgtcttt ggatcgatgt tggttatcac caccttcctg    720

caccacaacg acgaggagac cccttggtac gccgattccg agtggaccta cgtcaagggc    780

aacctctcgt ccgttgaccg ttcgtacggt gccctgatcg ataacctctc ccacaacatc    840

ggcacccacc agattcacca cctgttcccc atcattcctc actacaagct caagaaggct    900

accgccgctt tccaccaggc ctttcccgag ctggtccgca agtcggacga gcctatcatt    960

accgctttct ttcgcgtcgg ccgtctctac gccaactacg gtgtcgttga tcccgaggct   1020

aagttgttca ccctgaagga agccaaggcc gctaacgagg ccgctgtcaa gaccaagtcc   1080

acctaa                                                              1086
```

<210> SEQ ID NO 33
<211> LENGTH: 361
<212> TYPE: PRT
<213> ORGANISM: Phytophthora parasitica

<400> SEQUENCE: 33

```
Met Ala Thr Lys Gln Ala Tyr Val Phe Pro Thr Leu Thr Glu Ile Lys
1               5                   10                  15

Arg Ser Leu Pro Ser Glu Cys Phe Glu Ala Ser Val Pro Leu Ser Leu
            20                  25                  30

Tyr Tyr Thr Val Arg Cys Leu Val Ile Ala Val Ala Leu Ala Phe Gly
        35                  40                  45

Leu Asn Tyr Ala Arg Gly Leu Pro Val Val Glu Asn Leu Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Ile His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Ile Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Phe Ala Tyr Leu Ile Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Ile Phe Val Phe Gly Ser Met Leu Val Ile Thr Thr Phe Leu
225                 230                 235                 240
```

```
His His Asn Asp Glu Glu Thr Pro Trp Tyr Ala Asp Ser Glu Trp Thr
            245                 250                 255

Tyr Val Lys Gly Asn Leu Ser Ser Val Asp Arg Ser Tyr Gly Ala Leu
        260                 265                 270

Ile Asp Asn Leu Ser His Asn Ile Gly Thr His Gln Ile His His Leu
    275                 280                 285

Phe Pro Ile Ile Pro His Tyr Lys Leu Lys Lys Ala Thr Ala Ala Phe
    290                 295                 300

His Gln Ala Phe Pro Glu Leu Val Arg Lys Ser Asp Glu Pro Ile Ile
305                 310                 315                 320

Thr Ala Phe Phe Arg Val Gly Arg Leu Tyr Ala Asn Tyr Gly Val Val
            325                 330                 335

Asp Pro Glu Ala Lys Leu Phe Thr Leu Lys Glu Ala Lys Ala Ala Asn
        340                 345                 350

Glu Ala Ala Val Lys Thr Lys Ser Thr
    355                 360


<210> SEQ ID NO 34
<211> LENGTH: 23
<212> TYPE: DNA
<213> ORGANISM: Artificial Sequence
<220> FEATURE:
<223> OTHER INFORMATION: It is synthesized.

<400> SEQUENCE: 34

cacacacaaa cctctctccc act                                              23


<210> SEQ ID NO 35
<211> LENGTH: 26
<212> TYPE: DNA
<213> ORGANISM: Artificial Sequence
<220> FEATURE:
<223> OTHER INFORMATION: It is synthesized.

<400> SEQUENCE: 35

caaatgaacg tatcttatcg agatcc                                           26


<210> SEQ ID NO 36
<211> LENGTH: 18
<212> TYPE: DNA
<213> ORGANISM: Artificial Sequence
<220> FEATURE:
<223> OTHER INFORMATION: It is synthesized.

<400> SEQUENCE: 36

tcttccccac cctcaccg                                                    18


<210> SEQ ID NO 37
<211> LENGTH: 20
<212> TYPE: DNA
<213> ORGANISM: Artificial Sequence
<220> FEATURE:
<223> OTHER INFORMATION: It is synthesized.

<400> SEQUENCE: 37

caagccacga gcgtagttca                                                  20


<210> SEQ ID NO 38
<211> LENGTH: 24
<212> TYPE: DNA
<213> ORGANISM: Artificial Sequence
<220> FEATURE:
<223> OTHER INFORMATION: It is synthesized.
```

-continued

```
<400> SEQUENCE: 38

cgtactaccg attgaatggc ttag                                              24


<210> SEQ ID NO 39
<211> LENGTH: 23
<212> TYPE: DNA
<213> ORGANISM: Artificial Sequence
<220> FEATURE:
<223> OTHER INFORMATION: It is synthesized.

<400> SEQUENCE: 39

cctacggaaa ccttgttacg act                                               23
```

PARASITIC PHYTOPHTHORA-DERIVED OMEGA-3 FATTY ACID DESATURASE FOR SYNTHESIZING POLYUNSATURATED FATTY ACIDS, CARRIER CONTAINING FATTY ACID DESATURASE, RECOMBINANT MICROORGANISMS, AND APPLICATION THEREOF

The present invention claims the priority of Chinese Patent Application No. CN 2015109025795 filed Dec. 9, 2015, and No. CN 201610184669X filed Mar. 28, 2016.

TECHNICAL FIELD

The invention is in the field of biotechnology engineering. It relates to the use of microbes to synthesize polyunsaturated fatty acids (PUFAs), in particular to an ω-3 fatty acid desaturase for the synthesis of PUFAs, a plasmid containing the ω-3 fatty acid desaturase, a recombinant microorganism containing the plasmid and its application.

BACKGROUND OF THE INVENTION

Long chain polyunsaturated fatty acids (LC-PUFAs) are PUFAs containing 20 or more than 20 carbon atoms, which can be divided into ω-6 and ω-3 according to the position of the first double bond distance at the C end. ω-3 LC-PUFAs can not be synthesized in human body. It needs to be obtained from diet. It belongs to essential fatty acids, such as EPA and DHA. It is found that ω-3 LC-PUFAs, represented by EPA and DHA, can be used as precursors to synthesize some hormones, with multiple physiological functions and potential medicinal value. So far, the source of ω-3 LC-PUFAs is mainly deep-sea fish, but the LC-PUFAs extracted from it has the disadvantages of poor stability, complex purification process, easy oxidation and so on. In recent years, microorganisms, as a new source of LC-PUFAs, are attracting more and more attention. Marine algae grow through autotrophic, heterotrophic and mixed nutrition and have short growth cycles. It is a primary producer of EPA and DHA and one of the most potential sources of ω-3 LC-PUFAs. Yeast and mold are low in research cost and suitable for mass production. They possess the potential of producing multiple LC-PUFAs. With the rapid development of molecular biology and biotechnology, more and more attention has been paid to the oleaginous fungi in order to produce EPA and DHA through the pathway of fatty acid synthesis in the genetically engineered fungi. However, due to low efficiency and so on, it has not yet been commercialized.

In nature, the synthesis of ω-3 LC-PUFAs is usually initiated by LA and ALA, and finally synthesized into EPA and DHA after a series of enzyme catalysis. Among them, ω-3 fatty acid desaturase is one of the key enzymes in the synthesis of ω-3 LC-PUFAs. It has three histidine rich domains, which can catalyze ω-6 PUFAs to produce corresponding ω-3 PUFAs, such as LA (C18:2), GLA (C18:3), DGLA (C20:3) and ARA (Arachidonic, or written as AA) to ALA (C18:3), SDA (C18:4), ETA (C20:4) and EPA (C20:5).

It is found that ω-3 fatty acid desaturase from different sources has different catalytic efficiency for fatty acids with different carbon chain lengths. At present, known ω-3 fatty acid desaturase derived from algae and plants can only catalyze 18C ω-6 PUFAs such as LA and GLA. The ω-3 fatty acid desaturase FAT 1 derived from the *Caenorhabditis elegans* can simultaneously use 18C and 20C PUFAs as substrates, but the catalytic activity of 20C PUFAs substrates is very low. Subsequently, Pereira (et al.) found that ω-3 fatty acid desaturase sdd17 from *Saprolegnia diclina* has no catalytic activity for 18C PUFAs, but can catalyze 20C ARA to EPA, and the conversion rate is 25.9%. Similarly, ω-3 fatty acid desaturase OPIN 17 from *Phytophthora infestans* can not use 18C PUFAs as substrate, but the conversion rate of ARA is 30.94%.

In recent years, Xue (et al.) have isolated three ω-3 fatty acid desaturase, PaD 17 from *Pythium aphanidermatum*, PsD 17 from *Phytophthora sojae* and PrD 17 from *Phytophthora ranmorum*, and have heterologous expression in recombinant yeast (Identification and characterization of new Δ-17 fatty acid desaturases, Appl Microbiol Biotechnol (2013) 97:1973-1985). These three enzymes not only catalyze 18C PUFAs but also catalyze 20C PUFAs, and prefer to catalyze 20C substrate ARA. Through further study of these fatty acid desaturase, it is found that they have high conversion rate to ARA at normal temperature, so the biological accumulation of EPA at normal temperature is realized. This kind of fatty acid desaturase preference uses 20C ω-6 LC-PUFAs as substrate to catalyze the synthesis of ω-3 LC-PUFAs, so they can catalyze ARA to produce EPA directly and efficiently, which is of great significance for the production of ω-3 LC-PUFAs by biosynthetic method. In order to improve the production efficiency, it is particularly important to screen the fatty acid desaturase which can efficiently synthesize EPA.

On the other hand, *Mortierella alpina* is an oleaginous fungus with a lipid accumulation that can reach 50% of the stem weight of the cell. It has been applied to the industrial production of Arachidonic acid (AA, C20:4), and its edible oil has been evaluated by the safety of FDA. In addition to synthesizing AA, *Mortierella alpina* also has certain ability to synthesize Eicosapentanoic acid (EPA, C20:5). EPA belongs to ω-3 long chain polyunsaturated fatty acids (LC-PUFAs), which plays an important role, such as promoting the development of the mammalian brain and the formation and repair of nerve tissue, and preventing asthma, cancer, depression, obesity, immune disorder, and cardiovascular disease. But these fatty acids can not be synthesized by human body, and they need to be absorbed from foods rich in ω-3 LC-PUFAs (such as deep-sea fish oil). Owing to overfishing and environmental pollution, the ω-3 LC-PUFAs provided by deep-sea fish is unable to meet the demand of the market, the production of ω-3 LC-PUFAs by microorganism has become a research hotspot.

However, obtaining an oleaginous fungus with higher EPA yield, especially *Mortierella alpina*, remains the expectation of technicians in this field.

SUMMARY OF THE INVENTION

The object of the present invention is to construct recombinant yeast and alpine spores through some ω-3 fatty acid desaturase (or ω-3 desaturase in brief) with a preference for 20 C at normal temperature. A fatty acid desaturase was obtained by identifying each ω-3 fatty acid desaturase catalyzed by ARA to produce EPA, which could yield a high yield of 20 C ω-6 LC-PUFAs into ω-3 LC-PUFAs.

The idea of this invention is to compare sequences of 5 kinds of known ω-3 fatty acid desaturase with a preference for 20 C at normal temperature. According to sequence similarity and homology analysis, the gene (sequence as SEQ ID NO. 1) from *Phytophthora parasitica* and the gene from *Aphanomyces invadans* (sequence as SEQ ID NO. 7) are selected to be similar to the known sequence. Clustal W2 was used to compare the amino acid sequence with the known sequences of the ω-3 fatty acid desaturase. It is found that the natural genes from *Phytophthora parasitica* (sequences as SEQ ID NO. 1) and the gene from *Aphanomyces invadans* (sequence as SEQ ID NO. 7) have 3 His-box regions similar to those of known sequences. The results of TMHMM analysis showed that these sequences had transmembrane domains similar to known sequences. Then the activity was verified.

Further, the invention constructs two segments of the ω-3 fatty acid desaturase sequence aimed at the optimized *Saccharomyces cerevisiae*, such as the oPpFADS17y of the SEQ ID NO. 3 (i.e. oPpFADS17 in CN 2015109025795, which is distinguished from the oPpFADS17 that is optimized for the *Mortierella alpina* in the CN 201610184669X. In the invention, the suffix "Y" or "m" is added respectively), and the oAiFADS17y of the SEQ ID NO. 9 (i.e. oAiFADS17 in CN 2015109025795, which is distinguished from the oAiFADS17 that is optimized for the *Mortierella alpina* in the CN 201610184669X. In the invention, the suffix "Y" or "m" is added respectively). PCR technique was used to amplify the target gene fragment and insert the pYES 2/NT C (i.e. PYES 2/NT C in CN 2015109025795) to obtain pYES2/NT C-oPpFADS17 (i.e. PYES2/NT C-oPpFADS17 in CN 2015109025795) and pYES2/NT C-oAiFADS17 (i.e. PYES2/NT C-oAiFADS17 in CN 2015109025795), and then transformed into *Saccharomyces cerevisiae* INVSc 1 to obtain recombinant *Saccharomyces cerevisiae* strains. It can successfully express the protein encoded by two segments of the gene. Then, by adding the PUFAs of different carbon chain lengths as substrates, the activity was verified, oPpFADS17y and oAiFADS17y were determined to have good activity.

The invention provides a coding sequence of ω-3 fatty acid desaturase with specific catalytic 20C capability, and its sequence is shown as SEQ ID NO. 3 and SEQ ID NO. 9 respectively.

The invention also provides expression vectors pUC57-oPpFADS17 and pUC57-oAiFADS17 containing SEQ ID NO. 3 and SEQ ID NO. 9 sequence respectively, which respectively express ω-3 fatty acid desaturase from *Phytophthora parasitica* and from *Aphanomyces invadans* respectively.

The invention also provides recombinant microorganism for expressing the ω-3 fatty acid desaturase from *Phytophthora parasitica* or from *Aphanomyces invadans* respectively. Preferably, the recombinant microorganism is *Saccharomyces cerevisiae.*

The invention provides ω-3 fatty acid desaturase oPpFADS17 and oAiFADS17 from *Phytophthora parasitica* and from *Aphanomyces invadans* respectively, which play a key role in the PUFAs biosynthesis pathway, such as SEQ ID NO. 4 and SEQ ID NO. 10.

The invention also provides the use of the above ω-3 fatty acid desaturase oPpFADS17y (i.e. oPpFADS17 in CN 2015109025795) and oAiFADS17y (i.e. oAiFADS17 in CN 2015109025795) in the biosynthesis of PUFAs, especially to catalyze $C20:4^{\Delta5,8,11,14}$ to $C20:5^{\Delta5,8,10,14,17}$ at normal temperature.

The two ω-3 fatty acid desaturase of the invention can catalyze 18C and 20C PUFAs, but is preferred to transform 20C ARA into EPA, and the catalytic efficiency reaches 65%. This technology laid the foundation for subsequent industrial production of EPA and DHA.

In addition, the invention also provides an engineered strain capable of producing large quantities of EPA under normal temperature. It is based on the method of the *A. tumefaciens* mediated, through the expression of the ω-3 fatty acid desaturase oPpFADS17m (i.e. oPpFADS17 in CN 201610184669X, which is distinguished from the oPpFADS17 in CN 2015109025795, so that the suffix "m" is added to the present invention to distinguish). The invention also relates to the recombinant *Mortierella alpina* used for industrial production of fatty acids, especially for the production of EPA.

Through the above study, the applicant expects to verify that over expression of ω-3 fatty acid desaturase from *Phytophthora parasitica* in *Mortierella alpina* can increase EPA production in *M. alpina*, and to obtain an engineering strain with high yield.

Therefore, the invention will transform the oPpFADS17m from *Phytophthora parasitica* into the *M. alpina* uracil auxotrophic strain, and construct a recombinant *M. alpina* with higher EPA yield at normal temperature, in which oPpFADS17m has been optimized for *M. alpina.*

In particular, the present invention provides a recombinant *M. alpina* for expressing the ω-3 fatty acid desaturase oPpFADS17m (i.e. oPpFADS17 in CN 201610184669X) from *Phytophthora parasitica*, which was preserved in China General Microbiological Culture Collection Center (CGMCC) since Jan. 18, 2016, with the accession number CGMCC No. 11820. The address of CGMCC is the Institute of Microbiology, Chinese Academy of Sciences, No. 1, Beichen West Road, Chaoyang District, Beijing, China.

In the present invention, the ω-3 fatty acid desaturase oPpFADS17m gene is derived from *Phytophthora parasitica*, which is optimized for *Mortierella alpina*, shown as SEQ ID NO.5 (Genbank accession No: KT372001), and its amino acid sequence is shown as SEQ ID No.6.

In the present invention, the recombinant *Mortierella alpina* is constructed by using the recombinant plasmid pBIG2-ura5s-oPpFADS17 containing the oPpFADS17m gene to convert *A. tumefaciens* and then to the *M. alpina* uracil auxotrophic strain with the *A. tumefaciens.*

According to a preferred embodiment, the *M. alpina* uracil auxotrophic strain is generated by inactivating the ura5 encoding orotate phosphoribosyltransferase (OPRTase) in *M. alpina* ATCC32222. Preferably, the *M. alpina* uracil auxotrophic strain is *M. alpina* MAU1, which was preserved in China General Microbiological Culture Collection Center (CGMCC) since Dec. 1, 2013, with the accession number CGMCC No. 8414. The address of CGMCC is the Institute of Microbiology, Chinese Academy of Sciences, No. 1, Beichen West Road, Chaoyang District, Beijing, China. It was also preserved in the laboratory of Jiangnan University, and was named CCFM501.

In order to obtain the above recombinant *M. alpina*, the invention also provides a method for constructing the strain, comprising the following steps:

(a) According to the natural origin of ω-3 fatty acid desaturase in *Phytophthora parasitica* (Genbank accession No: XM_008906963) and condon usage bias of *M. alpina*, artificially synthesizing the ω-3 fatty acid desaturase gene oPpFADS17m (oPpFADS17 in CN 201610184669.X), shown as SEQ ID NO.5 (Genbank accession No: KT372001);

(b) Constructing the recombinant plasmid pBIG2-ura5s-oPpFADS17;

(c) Transforming the obtained recombinant plasmid pBIG2-ura5s-oPpFADS17 into *A. tumefaciens;*

(d) Transforming *M. alpina* uracil auxotrophic strain with *A. tumefaciens* containing the recombinant plasmid pBIG2-ura5s-oPpFADS17;

(e) Screening and identifying the transformed strains and obtaining a special EPA producing recombinant *M. alpina* with overexpression of ω-3 fatty acid desaturase oPpFADS17m.

Preferably, in step (c), *A. tumefaciens* is *A. tumefaciens* C58C1.

In step (d), *M. alpina* uracil auxotrophic strain is *M. alpina* MAU1 (CGMCC No. 8414). It was also named CCFM501 in the laboratory of Jiangnan University.

In step (e), screening and identifying of transformed strains include the following steps:

(1) Scouring the surface of GY medium with 3 mL saline, and collecting liquid in a sterile 1.5 mL centrifuge tube and then filtering with 25 μm filter membrane;

(2) Counting the spore concentration with a haemacytometer and adjusting the concentration to $10^8$/100 μL, $10^6$/100 μL and $10^4$/100 μL each, and each with 200 μL coating on the GY-CS tablet containing 100 μg/mL of spectinomycin and 100 μg/mL cefotaxime, and then culturing at 25° C. for 2-3 days in the dark;

(3) Picking the fungal mycelium by sterile forceps and placing them on a SC-CS plate containing 100 μg/mL of the spectinomycin and 100 μg/mL cefotaxime, and then culturing at 25° C. for 2-3 days in the dark;

(4) Observing the growth of *M. alpina* on the plate, and picking the mycelium on the SC-CS plate onto the GY slope;

(5) Culturing the *M. alpine* strain spores in the above step 4) on the GY medium for 3 times;

(6) Identifying the strains with hereditary stability as recombinant *M. alpina* with overexpression of ω-3 fatty acid desaturase oPpFADS17m, and keeping it on the GY slope;

(7) Extracting the genomic DNA of the recombinant *M. alpine*, and designing a pair of primers with specific promoters and terminators for PCR verification;

```
P1 (sense):
CACACACAAACCTCTCTCCCACT

P2 (antisense):
CAAATGAACGTATCTTATCGAGATCC;
```

(8) Keeping the recombinant *M. alpina* on the GY slope.

The invention also provides the use of the above-mentioned recombinant *M. alpina* in the production of fatty acids, especially EPA.

In the present invention, the construction of recombinant plasmid pBIG2-ura5s-oPpFADS17 can be referred to the Chinese patent application CN 201310524221.4.

In the present invention, the *M. alpina* uracil auxotrophic strain is *M. alpina* MAU1 with the accession number CGMCC No. 8414. The strain has been published in Chinese patent application CN 201310347934.8.

According to the specification of CN 201310347934.8, the construction of *M. alpina* MAU1 was as follows: Inactivate the *M. alpina* ura5 gene through deletion of the 18 bp (213 bp to 230 bp) DNA sequence by homologous recombination. The homologous DNA arms are the 1393 bp (from −1180 bp to +212 bp) upstream and the 1362 bp (from +231 bp to +1592 bp) down-stream of the ura5 gene. The detailed steps are described as follows: obtaining the ura5 knockout DNA fragment; constructing the knockout plasmid pBIG4KOura5; transformation of *A. tumefaciens* using pBIG4KOura5; ATMT of *M. alpina* using *A. tumefaciens* C58C1-pBIG4KOura5 (CGMCC No. 7730); screening and identifying uracil auxotroph to obtain uracil auxotrophic strains.

In the present invention, the *A. tumefaciens* used is *Agrobacterium tumefaciens* C58C1 (Tsuji G, Fujii S, Fujihara N, et al. *Agrobacterium tumefaciens*-mediated transformation for random insertional mutagenesis in *Colletotrichum lagenarium*[J]. Journal of General Plant Pathology, 2003, 69(4): 230-239.).

Based on the transformation system of *M. alpina*, the invention uses the transformation of *A. tumefaciens* to obtain a recombinant *M. alpina* for expressing the ω-3 fatty acid desaturase oPpFADS17m from *Phytophthora parasitica*. The recombinant *M. Alpina* had been passed through several generations, and the oPpFADS17m fragment remained stable in the genome, and the growth characteristics of the strains were not significantly different from the primary strains, but the EPA yield of the recombinant strain reached 31.5% of the total fatty acid, and the conversion rate to AA was up to 77.6%, while the primary strain was almost not detected in the original strain. The recombinant *M. Alpina* of the present invention has a significant increase in EPA yield than other heterogenous ω-3 fatty acid desaturase gene recombinant *M. Alpina* and even MA-oPaFADS17-3. The invention further promotes the progress of oleaginous fungus industry and the industrialized production of EPA.

Information on preservation of biomaterials: *M. alpina* MA-oPpFADS17-4 was preserved in China General Microbiological Culture Collection Center (CGMCC) since Jan. 18, 2016, with the accession number CGMCC No. 11820. The address of CGMCC is the Institute of Microbiology, Chinese Academy of Sciences, No. 1, Beichen West Road, Chaoyang District, Beijing, China.

DESCRIPTION OF THE ATTACHED DRAWINGS

FIG. 1 is the target gene fragment of PCR amplification, in which M is Marker, Lane 1 is oPaFADS17 gene fragment (1080 bp), Lane 2 is oPpFADS17y gene fragment (1086 bp), and Lane 3 is oAiFADS17y gene fragment (1095 bp);

FIG. 2 is the schematic diagram of recombinant *Saccharomy cescerevisiae*, in which M is Marker, Lane 1 is a carrier containing empty plasmid, Lane 2-4 is the 1, 2, 3 transformants of INVSc 1-oPaFADS17; Lane 5-7 is the 1, 2, 3 transformants of INVSc 1-oPpFADS17; Lane 8-10 is the 1, 2, 3 transformants of INVSc 1-oAiFADS17.

FIG. 3 is the transcriptional level of the *Saccharomyces cerevisiae* transformants, in which Lane 1 is a carrier containing empty plasmid, Lane 2-4 is the 1, 2, 3 transformants of INVSc 1-oPpFADS17; Lane 5-7 is the 1, 2, 3 transformants of INVSc 1-oAiFADS17; Lane 8-10 is the 1, 2, 3 transformants of INVSc 1-oPaFADS17.

Figure 6:
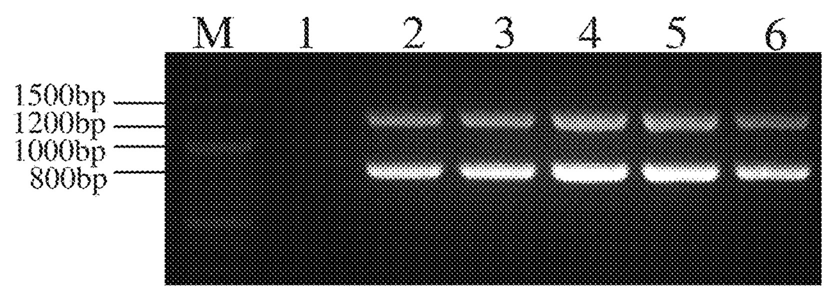
Figure 7:
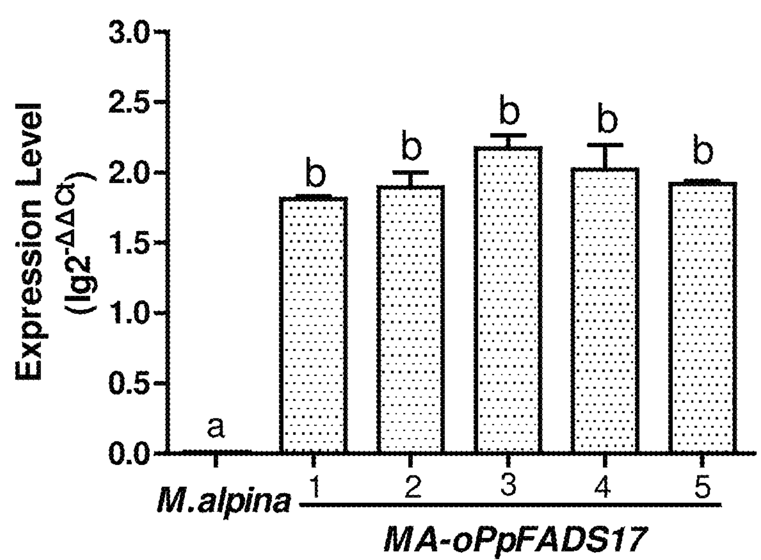

FIG. 6 is the schematic diagram of agarose gel electrophoresis of identification of the recombinant *M. Alpina* that overexpress oPpFADS17m gene, in which M is marker; 1 is negative control; 2-6 is No. 1-5 transformant FIG. 7 is the expression level of ω-3 fatty acid desaturase gene of wild type *M. alpina* and 5 recombinant *M. alpine*, in which, *M. alpina* is wild type *M. alpina* (control); 1-5 are representative of recombinant *M. alpine* MA-oPpFADS17-

1, MA-oPpFADS17-2, MA-oPpFADS17-3, MA-oPpFADS17-4, and MA-oPpFADS17-5.

EMBODIMENTS

The following Embodiments further illustrate the present invention. The experimental methods without indicating specific conditions in the followings examples will be performed generally in accordance with the manual of molecular cloning experiments.

The present invention relates to the following medium:

Broth medium: 20 g/L glucose, 5 g/L yeast extract, 1 g/L potassium dihydrogen phosphate, 0.25 g/L magnesium sulfate heptahydrate, 10 g/L potassium nitrate, pH 6.

MM solid medium: 1.74 g/L potassium hydrogen phosphate, 1.37 g/L potassium dihydrogen phosphate, 0.146 g/L sodium chloride, 0.49 g/L magnesium sulfate heptahydrate, 0.078 g/L calcium chloride, 0.0025 g/L ferrous sulfate, 0.53 g/L ammonium sulfate, 1.8 g/L glucose, 0.5% glycerol, 20 g/L agar, pH 6.8.

The IM medium was a MM medium containing additional 200 μM acetyl syringone (AS).

SC solid medium: 20 g/L glucose, 5 g/L yeast nitrogen source (without amino acid and ammonium sulfate), 1.7 g/L ammonium sulfate, 60 mg/L isoleucine, 60 mg/L leucine, 60 mg/L phenylalanine, 50 mg/L threonine, 40 mg/L lysine, 30 mg/L tyrosine, 20 mg/L adenine, 20 mg/L arginine, 20 mg/L histidine, 10 mg/L methionine, 20 g/L agar, pH 6.8

The SC-CS medium is a SC solid medium with 100 μg/mL Spectinomycin and 100 μg/mL Cefotaxime Sodium.

SC selective medium: 6.7 g/L yeast nitrogen source (without amino acid, while with ammonium sulfate), 20 g/L glucose, 0.1 g/L (respectively, adenine, arginine, cysteine, leucine, lysine, threonine and tryptophan), and 0.05 g/L (respectively, aspartic acid, histidine, isoleucine, methionine, phenylalanine, proline, serine, tyrosine and valine), 20 g/L agar powder.

GY solid medium: 20 g/L glucose, 10 g/L yeast extract, 2 g/L potassium nitrate, 1 g/L phosphate dihydrogen sodium, 3 g/L magnesium sulfate heptahydrate, 20 g/L agar, pH 6.8.

The GY-CS medium was a GY solid medium containing additional 100 μg/mL Spectinomycin and 100 μg/mL Cefotaxime Sodium.

SOC resuscitation medium: 20 g/L peptone, 5 g/L yeast powder, 0.5 g/L NaCl, 2.5 mM KCl, 10 mM $MgCl_2$, 20 mM glucose.

LB solid medium: 10 g/L peptone, 5 g/L yeast powder, 10 g/L NaCl, 20 g/L agar.

YPD medium: 10 g/L yeast extract, 20 g/L peptone, 20 g/L glucose. 20 g/L agar is added when a solid medium is involved.

1 Recombinant *S. cerevisiae* Expressing the ω-3 Fatty Acid Desaturase from *Phytophthora parasitica*

Example 1: Determination of ω-3 Fatty Acid Desaturase with a Preference for 20C at Normal Temperature Five kinds of known ω-3 fatty acid desaturase sequences (gene OPIN 17, SDD 17, PsD 17, PrD 17 and PaD 17) with a preference for 20C at normal temperature were compared in NCBI library. According to the analysis of sequence similarity and homology, two gene sequences of ω-3 fatty acid desaturase, which were similar to the known sequences, were screened out. They were derived from *Phytophthora parasitica* and *Aphanomyces invadans* respectively. The gene numbers are XM_008906963 and XM_008870610, respectively. According to the interpretation of the NCBI library, these two sequences belong to fatty acid desaturase, but there is no more detailed comments on their specific function.

Clustal W2 was used to compare the amino acid sequence with 5 kinds of known ω-3 fatty acid desaturase sequences. It is found that the natural genes from *Phytophthora parasitica* and the gene from *Aphanomyces invadans* have 3 His-box regions. The similar His-box region protein sequence is shown in the table 1. The results of TMHMM analysis showed that the two sequences had transmembrane domains similar to known sequences.

TABLE 1 amino acid sequences of 3 His-box regions of ω-3 fatty acid desaturase with a preference for 20 C. at normal temperature.

| species | Gene Name | Gene number | His-box I | His-box II | His-box III |
|---|---|---|---|---|---|
| *Phytophthora infestans* | OPIN 17 | CAJ30870 | HDAGH | HRHHH | HQIHH |
| *Saprolegnia diclina* | sdd 17 | AY373823 | HDCGH | HRHHH | HQVHH |
| *Phytophthora sojae* | PsD 17 | FW362214.1 | HDAGH | HRHHH | HQIHH |
| *Phytophthora ramorum* | PrD 17 | FW362213.1 | HDAGH | HRHHH | HQIHH |
| *Pythium aphanidermatum* | PaD 17 | FW362186.1 | HDCGH | HRHHH | HQIHH |
| *Phytophthora parasitica* | Hypothetical protein | XM_008906963 | HDAGH | HEHHH | HQIHH |
| *AphaNomyces invadans* | Hypothetical protein | XM_008870610 | HDCGH | HRHHH | HQVHH |

Example 2: Construction of Recombinant Expression Vector

1. Obtaining the Target Gene

Because the codon usage bias of sequence derived from *Phytophthora parasitica, AphaNomyces invadans* and *Pythium aphanidermatum* are different from that of *Saccharomyces cerevisiae*, according to the codon usage bias of eukaryotes, codon optimization was performed by Genscript OptimumGene™ system. The optimized gene oPpFADS17y (oPpFADS17 in CN 2015109025795), oAiFADS17y (oAiFADS17 in CN 2015109025795) and oPaFADS17 (as a positive control) as SEQ ID NO. 3, SEQ ID 9, and 11 are respectively artificially synthesized, and then connected to carrier pUC57-simple (PUC57-simple in CN 2015109025795) to obtain pUC57-oPpFADS17, pUC57-oAiFADS17 and pUC57-oPaFADS17 respectively, which are preserved in *E. coli* Top 10.

Figure 1:
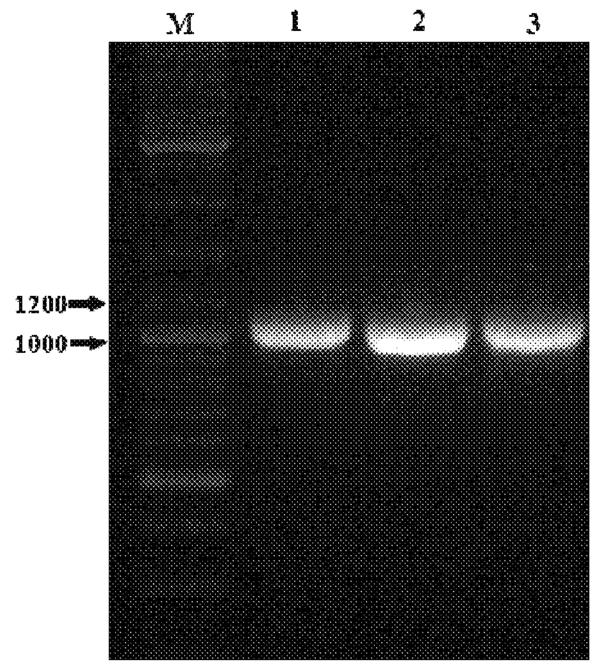

Primers were designed, and each pair of primers were added with enzyme sites EcoR I and Xho I (underline). The plasmid pUC57-oPpFADS17, pUC57-oAiFADS17 and pUC57-oPaFADS17 were used as templates, and the corresponding primers and KOD high fidelity polymerase were used to amplify the target gene by PCR. PCR program: 94° C. 30 s, 55° C. 30 s, 68° C. 1.5 min, 30 cycles, 68° C. 10 min. The PCR product was purified and the purified product was verified by agarose gel electrophoresis. The result is in FIG. 1.

The sequences of primers used to amplify the target gene are as follows:

```
oPpFADS17y F
ctaattgaattcATGGCAACCAAGCAAGC

oPpFADS17y R
cgattctcgagTTAAGTTGACTTGGTTTTAACAGCG

oAiFADS17y F
acaatggaattcATGCCATCCCCTAAAGCCAC

oAiFADS17y R
cctgatctcgagTTATAAGGTCTTTTTAACTGAGTTTGCTCT

oPaFADS17 F
catgtagaattcATGGCTTCGTCCACCGTTG

oPaFADS17 R
ttacgactcgagTTAGTTAGCCTTGGTCTTGGCAG
```

2. Enzyme Digestion Reaction:

At the temperature of 37° C., the target fragment and vector pYES2/NT C (PYES2/NT C in CN 2015109025795) are digested with the restrictive endonuclease EcoR I and Xho I. Enzyme digestion system: 2 μL EcoR I, 2 μL Xho I, 30 μL target gene/vector, 10 μL cutsmart Buffer, 56 μL deionized water, incubating at 37° C. for 12 h. The digestion products thus obtained were recovered with Thermo Scientific GeneJET gel extraction kit before preserved at −20° C.

In which, endonuclease buffer solution 10×cutsmart Buffer: 500 mM potassium acetate, 200 mM Tris-acetate buffer, 100 mM magnesium acetate, 1000 g/mL bovine serum albumin, pH 7.9.

3. Ligation Reaction:

The purified target fragment oPpFADS17y, oAiFADS17y and oPaFADS17 and vector pYES2/NT C were ligated with T4 ligase respectively, and then incubated at 4° C. for 12 h. The ligation system is: 1 μL vector pYES2/NT C (50 ng/L), 75-150 ng fragment, 1 μL buffer, 1 μL T4 ligase, with addition of water to 10 μL.

In which, 10×ligase buffer: 660 mM Tris-hydrochloric acid buffer (pH 7.6), 66 mM magnesium chloride, 100 mM DTT, 1 mM adenosine triphosphate.

4. Transformation of *Escherichia coli* TOP 10 Competent Cell

The method for transforming is as follows:

(1) In the aseptic state, 100 μL of the competent cells were taken, and 1-2 μL ligation product was added and the mixture was blown and mixed well.

(2) The competent cells in the above steps were moved into the electric rotating cup to avoid bubbles.

(3) The rotating cup was put into Bio-Rad electric rotary instrument and adjusted into a propriate preset program position. The electrical transformation was carried out according to the operation instructions of the instrument at the voltage condition of 1.8 kV.

(4) The transformed competent cells were transferred into a centrifugation tube containing 1 mL SOC medium and incubated for 1 h at 37° C. and 150 rpm.

(5) A LB solid medium plate containing 100 μg/mL ampicomycin was coated with 200 μL of the obtained product, and reversed and incubated at 37° C. overnight.

The positive transformants were picked up, the plasmids were extracted and sequenced, and the sequencing results were completely matched with the gene sequences, indicating that the ligation was successful and the expression vectors were obtained, named pYES2/NT C-oPpFADS17, pYES2/NT C-oAiFADS17, pYES2/NT C-oPpFADS17 respectively.

A *Saccharomyces cerevisiae* INVSc 1 (purchased from Invitrogen, USA) was cloned in 10 mL YPD medium and cultivated at 30° C. overnight. $OD_{600}$ was measured and transferred to a 50 mL medium to make the OD value being 0.4, then for another 2-4 h. It was centrifuged at 2500 RPM for 3 min, and 40 mL 1×TE suspension. Then at 2500 RPM centrifugation for 3 min, 2 mL 1×LiAc/0.5×TE suspension, incubated for 10 min at room temperature.

For each transformant of example 2, the 1001 of yeast suspension in the last step was added to the transformants, and 1 μg recombinant plasmid vector DNA and 100 μg salmon sperm carrier DNA were added. In order to get the best conversion efficiency, the carrier DNA was denatured repeatedly before each transformation, with boiling water bath for 2 min and ice bath for 2 min, repeated four times.

In which, 1×TE: 10 mM Tris-hydrochloric acid buffer (PH=8.0), 1 mM EDTA (PH=8.0); 1×LiAc:10 mM lithium acetate.

Example 4: PCR Verification of *Saccharomyces cerevisiae* Transformant

The corresponding primers were used for PCR identification. The primers are as follows:

```
T7
TAATACGACTCACTATAGGG

T7 terminator
TCGGTTAGAGCGGATGTG
```

PCR reaction system are as follows: 7 μL dd $H_2O$, 10 μL 10×Taq MIX, 1 μL universal primer T7, 1 μL universal primer T7 terminator, 1 μL templates (plasmids). The conditions of the PCR reaction are: 94° C. 5 min, 94° C. 30 s, 58° C. 30 s, 72° C. 1.5 min, 30 cycles, 72° C. 7 min.

Figure 2:
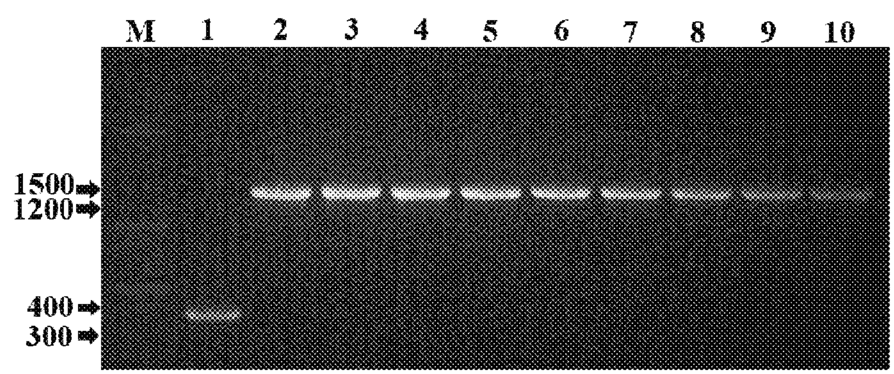

As shown in FIG. 2, 3 transformants were obtained from each gene. The recombinant transformants were named INVSc 1-oPpFADS17-1, -2, -3, and INVSc 1-oAiFADS17-1, -2, -3, and INVSc 1-oPaFADS17-1, -2, -3 respectively, and stored in 30 wt % glycerol tube. PYES2/NT C empty vector without gene fragment was used as negative control group.

Example 5: Inducible Culture of *Saccharomyces cerevisiae* Transformant

The single colony on the transformant plate of *Saccharomyces cerevisiae* was seeded on the seed medium SC-U, incubated at 28° C. for 48 h, and the $OD_{600}$ value was measured. Then it was transferred to the induction medium, and the OD value reached 0.4, while the exogenous polyunsaturated fatty acids substrate with different carbon chain lengths were added. It was incubated at 28° C. for 48 h and the bacteria were then collected.

In which, seed medium SC-U is: 6.7 g/L yeast nitrogen source (without amino acid but with ammonium sulfate), 20 g/L glucose, 0.1 g/L (adenine, arginine, cysteine, leucine, lysine, threonine, tryptophan and uracil, respectively), and 0.05 g/L (aspartic acid, histidine, isoleucine, methionine, phenylalanine, proline, serine, tyrosine and valine, respectively)

Induction medium is the seed culture medium in which the carbon source is replaced to 10 g/L raffinose and 20 g/L inducer galactose are added.

Example 6: Determination of Transcriptional Level of *Saccharomyces cerevisiae* Transformant The total RNA of *Saccharomyces cerevisiae* transformants was extracted, comprising:

(1) Appropriate amount of bacteria frozen in liquid nitrogen was removed, and liquid nitrogen was added to the precooled aseptic and enzyme-free mortar and ground well (2) 1 mL TRIzol (purchased from Invitrogen, USA) were added and continued to grind to powder and then put at the room temperature to dissolve.

(3) An enzyme free gun head was used to extract 1 mL of the above liquid in an enzyme free centrifuge tube and mixed with 200 μL of trichloromethane.

(4) Centrifuged at 12000 rpm and 4° C. for 15 min, and the supernatant was sucked in a new enzyme free centrifuge tube.

(5) Mixed with 200 μL trichloromethane, and centrifuged at 12000 rpm and 4° C. for 15 min, and the supernatant was sucked in a new enzyme free centrifuge tube.

(6) Equal volume of isopropanol was added and rest for 15 min, then centrifuged at 12000 RPM and 4° C. for 15 min. The supernatant was removed and then dried at room temperature.

(7) 1 mL 70 vol % ethanol was added, then centrifuged at 12000 RPM and 4° C. for 15 min. An enzyme free gun head was used to suck out ethanol and put it dry at room temperature.

(8) 50 μL enzyme free water was added to dissolve RNA and stored at −80° C.

(9) Determination of concentration: 1 μL RNA was taken and measured its concentration with NaNodrop 2000.

(10) Detecting of the integrity of RNA by denaturing gel electrophoresis: The integrity of RNA was observed by electrophoresis of 1 μg RNA in 1.2 wt % denaturing gel.

According to the gene sequence oPpFADS17y, oAiFADS17y and oPaFADS17 and internal standard 18S rDNA sequence of *Saccharomyces cerevisiae*, qRT-PCR primers were designed:

```
q-oPpFADS17y F
GGCAACCAAGCAAGCCTATGTA

q-oPpFADS17y R
GCTAAGGCAACTGCAATTACCAAAC

q-oAiFADS17y F
TACTACTTCGCTCCATTGTTCGTTT

q-oAiFADS17y R
CAACCGTAGGATCTATCAACTGAAG

q-oPaFADS17 F
CTTCGTCCACCGTTGCTG

q-oPaFADS17 R
AGCCAGCGATTCCGAGA
```

-continued

```
18S-F
AATCATCAAAGAGTCCGAAGACATTG

18S-R
CCTTTACTACATGGTATAACTGTGG
```

The total RNA of 0.5-1 μg was taken as the template, and the cDNA of the recombinant strain was obtained according to the operation of PrimeScript RT reagent kit (purchased from Japan TaKaRa company). ABI-Prism 7900 sequence detection system (Applied Biosystems, CA) was used to perform RT-qPCR reaction in accordance with the instructions of SYBR Green PCR Master Mix (Applied Biosystems, CA).

The reaction system is: 10 μl SYBR Green PCR Master Mix, 0.5 μl of each gene upstream and downstream primers, 8 μl enzyme free water, 1 μl template. The PCR cycle is set as 2 min at 50° C., 10 min at 95° C., 15 s at 95° C., 30 s at 60° C., and 40 cycles. The 18S rRNA of *Saccharomyces cerevisiae* is used as the internal reference gene.

According to the $2^{-\Delta\Delta Ct}$ method, the relative transcription level of the gene was calculated. All the samples were tested for three duplicates, in which: ΔΔCt=ΔCt (sample)−ΔCt (control).

Figure 3:
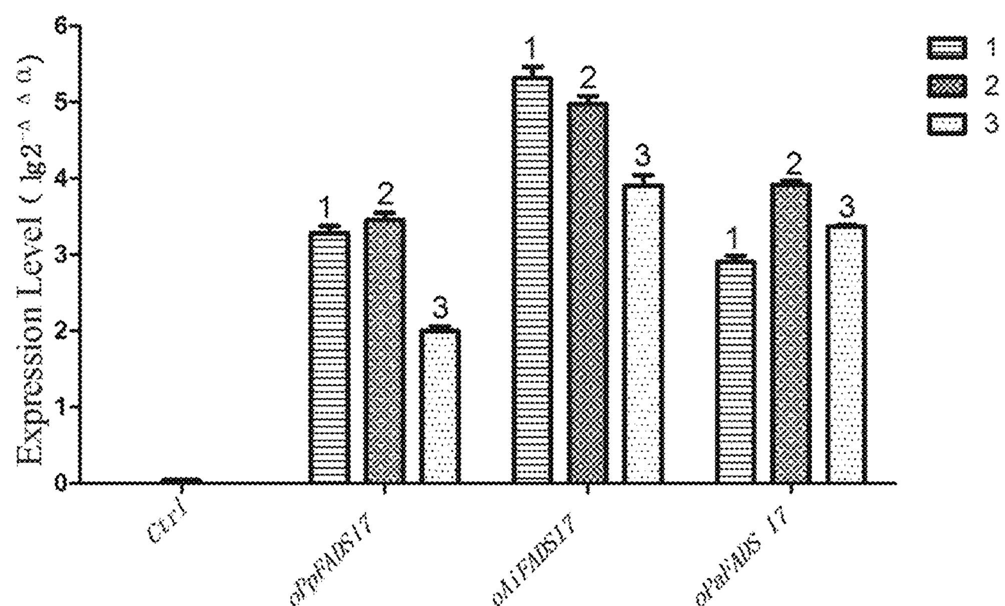

The result is shown in FIG. 3. It was found that, comparing each gene transformant to the control group, the value of ΔΔCt was about 10 in all gene transformants, which illustrated that the expression of the gene growing out of nothing, which showed that the gene was transcribed successfully in the host strain.

Example 7: Determination of Protein Expression in *Saccharomyces cerevisiae*

Under the same conditions, after inducing different transformants of different genes, the total protein was extracted from the broken mycelium with 0.5 mm acid-washed glass beads.

After the protein concentration was determined by BSA, SDS-PAGE electrophoresis was performed with sample volume of 100 μg total protein, until Marker was separated completely.

The protein in the gel was transferred to the PVDF membrane on the Bio-Rad electrophoresis apparatus. The transmembrane condition was 20 mA and overnight.

After the transmembrane was completed, the PVDF membrane was soaked in TBST buffer and incubated on the table concentrator for 10 min at room temperature. Repeat three times.

The PVDF membrane was soaked in TBST buffer containing 5 wt % skim milk and incubated on the table concentrator for 90 min at room temperature.

The PVDF membrane was soaked in TBST buffer and incubated on the table concentrator for 10 min at room temperature. Repeat three times.

In the ratio of 1:5000, anti-His primary antibody was dissolved in the TBST buffer containing 5 wt % skim milk, and then incubated on the table concentrator for 1 h.

The PVDF membrane was soaked in TBST buffer and incubated on the table concentrator for 10 min at room temperature. Repeat three times.

In the ratio of 1:10000, the goat anti-mouse secondary antibodies was dissolved in the TBST buffer containing 5 wt % skim milk, and then incubated on the table concentrator for 1 h.

The PVDF membrane was soaked in TBST buffer and incubated on the table concentrator for 10 min at room temperature. Repeat three times.

The PVDF film was developed by ECL, and exposed and photographed in the Western imager.

The results showed that different transformants of different genes were all expressed, and the protein expression level of different transformants was almost the same.

In which, TBST buffer (IL) consisted of 8.8 g HCl; 20 mL IM pH 8.0 Tris-HCl buffer; 0.5 mL Twain 20.

Example 8: Extraction of Fatty Acid from *Saccharomyces cerevisiae*

The following steps are included:

The induced bacteria were collected and then vacuum freeze-dried.

After fully ground and crushed, 10 mg of the above bacteria was weighed, 1 mL 10 wt % hydrochloric acid in methanol solution (i.e. methanol containing 10 wt % HCl) and internal standard (C15:0 and C21:0, each of 100 μl) were added, then mixed well with vibration for 3 h at 60° C. in water bath and vibrated every 0.5 h.

1 mL hexane and 1 mL saturated sodium chloride were added to mix evenly, and centrifuged at 4000 rpm for 5 min. The supernatant was taken into a clean bottle.

1 mL hexane was added to the original bottle and centrifuged at 4000 rpm for 5 min. The supernatant was taken into the above-mentioned new bottle.

The liquid in the new bottle is blown dry with N2. Then 1 mL hexane was added, the lid was tightened, and shaken and dissolved, thus obtained fatty acid methyl ester solution.

The obtained fatty acid methyl esters were analyzed by GC-MS (Shimadzu Co., Japan) and Rtx-Wax (30 m×0.25 mm, 0.25 m) as the chromatographic column. The mass spectrometry detection was under the temperature of the vaporization chamber and detector at 240° C. and 250° C. respectively. 1 μL samples were injected by distributary injection, the split ratio was 10:1, and the carrier gas was helium.

Temperature programmed: the initial temperature was 40° C. for 5 min, 20° C./min to 150° C., then 5° C./min to 190° C. for 5 min, and at last 5° C./min to 220° C., and for 17 min. Qualitative and quantitative analysis of fatty acids in samples was carried out by comparison of their retention time, peak area ratio and mass spectrometric analysis to those of fatty acid methyl ester standard (C15:0).

Figure 4:
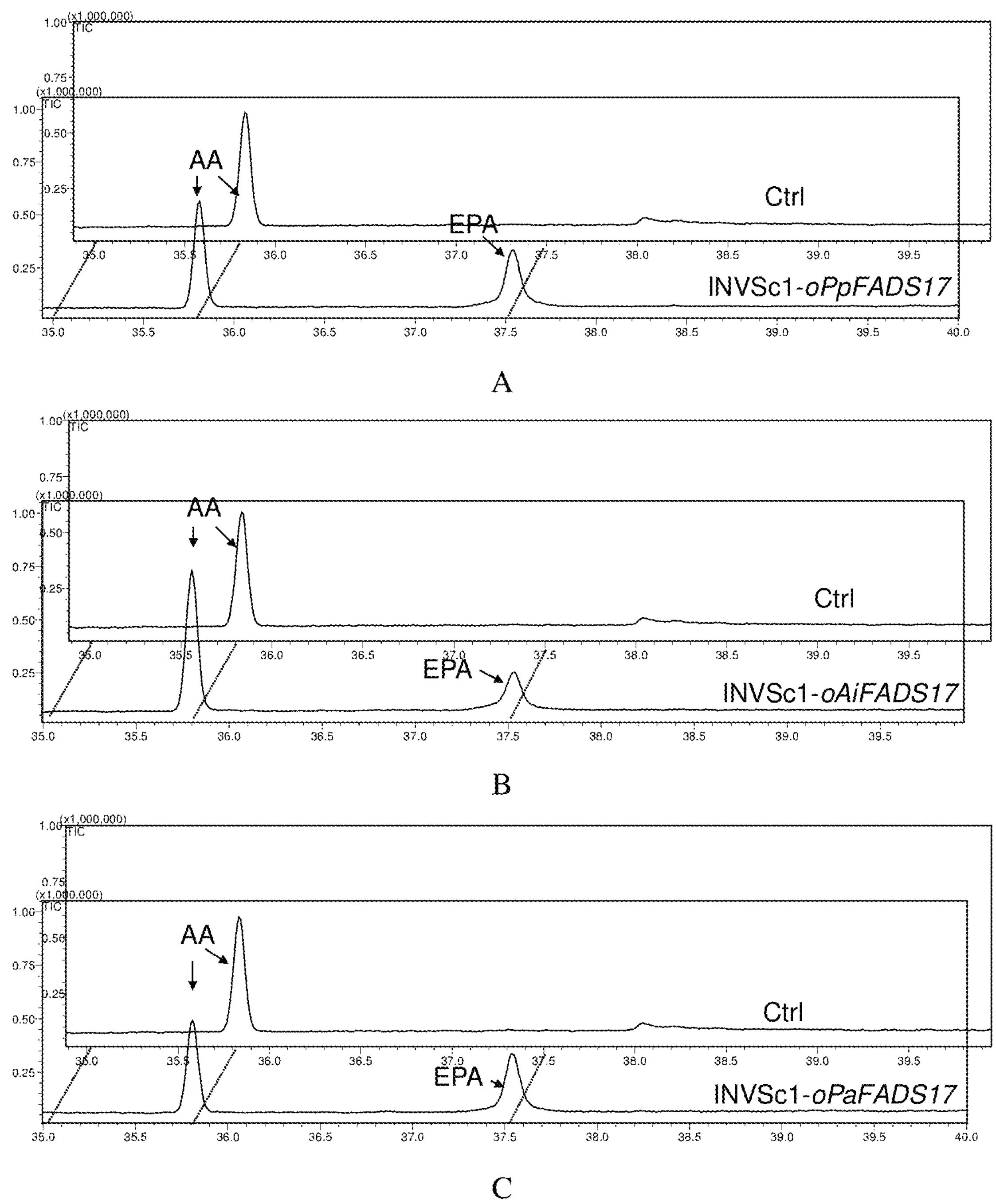
FIG. 4 is the result of gas phase detection of transformants of *Saccharomyces cerevisiae* in which A is INVSc 1-oPpFADS17, B is INVSc 1-oAiFADS17, and C is INVSc 1-oPaFADS17.
Figure 5:
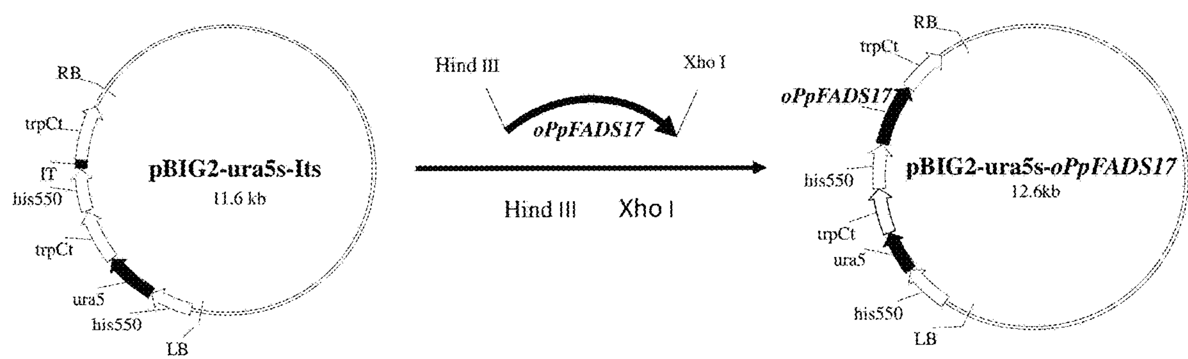
FIG. 5 is the schematic diagram of construction of the plasmid pBIG2-ura5 s-oPpFADS17.

Example 9: Identification of the Activity of ω-3 Fatty Acid Desaturase with a Preference for 20C at Normal Temperature In the induction medium, three ARA at concentration gradient of 0.05 mM, 0.1 mM and 0.2 mM were added as substrates to collect the bacteria and extract fatty acids. The results of GC-MS fatty acid determination were shown in FIG. 4.

Compared with the Ctrl group, INVSc 1-oPpFADS17, INVSc 1-oAiFADS17 and INVSc 1-oPaFADS17 had a new peak in 37.5 min. By comparison with fatty acid methyl ester standard products and mass spectrometric analysis, this peak was found to be EPA. The results of the specific analysis are shown in Table 2.

TABLE 2

Catalytic efficiency of different ω-3 fatty acid desaturase recombinant *Saccharomyces cerevisiae* recombinants on ARA

| Recombinant transformant (INVSc 1-) | 0.05 mM ARA EPA output (mg/g) | 0.05 mM ARA EPA conversion (100%) | 0.1 mM ARA EPA output (mg/g) | 0.1 mM ARA EPA conversion (100%) | 0.2 mM ARA EPA output (mg/g) | 0.2 mM ARA EPA conversion (100%) |
|---|---|---|---|---|---|---|
| oPpFADS17-1 | 9.0 ± 0.3 | 71.3 ± 3.5 | 6.6 ± 0.9 | 44.5 ± 3.7 | 5.6 ± 0.2 | 34.5 ± 1.2 |
| oPpFADS17-2 | 9.0 ± 0.1 | 63.3 ± 2.3 | 8.7 ± 1.0 | 48.7 ± 3.7 | 4.5 ± 0.5 | 28.0 ± 2.4 |
| oPpFADS17-3 | 9.4 ± 0.5 | 64.8 ± 3.3 | 7.8 ± 3.4 | 49.0 ± 2.3 | 3.3 ± 0.5 | 43.8 ± 2.5 |
| oAiFADS17-1 | 5.7 ± 0.4 | 41.4 ± 2.4 | 3.8 ± 0.7 | 26.1 ± 1.0 | 3.7 ± 0.7 | 27.0 ± 1.0 |
| oAiFADS17-2 | 6.7 ± 0.3 | 36.5 ± 3.0 | 6.2 ± 0.4 | 34.8 ± 0.8 | 3.3 ± 0.2 | 23.5 ± 2.3 |
| oAiFADS173 | 7.6 ± 0.6 | 46.3 ± 3.5 | 5.1 ± 0.7 | 33.5 ± 3.0 | 4.0 ± 0.2 | 23.9 ± 0.9 |
| oPaFADS17-1 | 8.5 ± 0.3 | 69.7 ± 1.7 | 6.3 ± 0.8 | 48.4 ± 2.9 | 3.1 ± 0.2 | 39.5 ± 2.8 |
| oPaFADS17-2 | 6.6 ± 0.4 | 67.9 ± 2.8 | 7.1 ± 0.7 | 46.8 ± 1.8 | 5.6 ± 0.6 | 23.1 ± 1.9 |
| oPaFADS17-3 | 6.2 ± 0.5 | 66.3 ± 3.3 | 6.7 ± 0.6 | 44.4 ± 2.7 | 4.1 ± 0.4 | 28.7 ± 0.8 |
| Ctrl | 0 ± 0 | 0 ± 0 | 0 ± 0 | 0 ± 0 | 0 ± 0 | 0 ± 0 |

The three transformants of INVSc 1-oPpFADS17 have the highest catalytic efficiency for ARA, of which INVSc 1-oPpFADS17-3 reached 64.8%, 49% and 43.8% respectively under three concentration gradients, which had almost no difference from the catalytic efficiency of the positive control INVSc 1-oPaFADS17 at three concentrations i.e. 69.7%, 48.4% and 39.5%, while the absolute yield is better than each of the transformants of the positive control.

In particular, in comparison with the recombinant lipoprotein yeast recorded in the existing technology "Identification and characterization of new Δ-17 fatty acid desaturases", in the realization of about the same catalytic conversion rate, the INVSc 1-oPpFADS17 transformant of the present invention had a significant reduction in the concentration of substrate ARA in the required inducible medium, in particular, the highest conversion rate under 0.05 mM, and a further increase in the output of EPA, and good EPA conversion capability. In addition, the expression vector used in the present invention only contains Δ9 fatty acid dehydrogenase, that is, only two kinds of monounsaturated fatty acids linoleic acid and palmitoleic acid in *Saccharomyces cerevisiae*. Compared with the existing recombinant lipolytic yeast, the recombinant *Saccharomyces cerevisiae* of the present invention will not interfere with the polyunsaturated fatty acid synthesis pathway to be used, and the recombinant vector of the present invention has His tags, which is more conducive to the purification and identification of subsequent proteins.

In addition, the above data showed that the ω-3 fatty acid desaturase gene (oAiFADS17y) sequence from *Aphanomyces invadans* was highly similar and closely relative to the ω-3 fatty acid desaturase gene (oPpFADS17y) sequence from *P. parasitica*, but the recombinant *Saccharomyces cerevisiae* obtained by the same technique had not the same effect. The catalytic efficiency of the transformant INVSc 1-oAiFADS17 from *Aphanomyces invadans* was relatively low, 46.3%, 33.5% and 23.9% respectively. In order to further verify whether these genes preferred to catalyze the 20C substrate, three recombinant transformants INVSc 1-oPpFADS17-3, INVSc 1-oAiFADS17-3 and INVSc 1-oPaFADS17-1 were selected, and 0.2 mM of LA, GLA, DGLA, ARA were added in the induced medium respectively, and 0.1 mM LA and 0.1 mM ARA were added at the same time, as shown in Table 3.

TABLE 3

Catalytic efficiency of different ω-3 desaturation *Saccharomyces cerevisiae* recombinant transformant on different substrates at 28° C.

| recombinant transformant (INVSc 1-) | 0.2 mM LA | | 0.2 mM GLA | | 0.2 mM DGLA | | 0.2 mM ARA | |
|---|---|---|---|---|---|---|---|---|
| | ALA output (mg/g) | ALA t (100%) | SDA output (mg/g) | SDA conversion (100%) | ETA output (mg/g) | ETA conversion (100%) | EPA output (mg/g) | EPA conversion (100%) |
| oPpFADS17-3 | 1.2 ± 0.1 | 7.1 ± 0.7 | 1.0 ± 0.1 | 4.7 ± 0.7 | 4.2 ± 0.2 | 25.6 ± 0.3 | 6.1 ± 0.6 | 45.3 ± 1.3 |
| oAiFADS17-3 | 0.5 ± 0.1 | 2.9 ± 0.4 | 0.3 ± 0.1 | 1.6 ± 0.3 | 3.0 ± 0.2 | 18.3 ± 0.4 | 3.8 ± 0.1 | 27.1 ± 1.1 |
| oPaFADS171 | 0.6 ± 0.1 | 3.4 ± 0.3 | 0.5 ± 0.1 | 3.0 ± 0.5 | 1.9 ± 0.3 | 13.4 ± 1.7 | 5.2 ± 0.5 | 49.5 ± 1.1 |
| Ctrl | 0 ± 0 | 0 ± 0 | 0 ± 0 | 0 ± 0 | 0 ± 0 | 0 ± 0 | 0 ± 0 | 0 ± 0 |

| recombinant transformant (INVSc 1-) | 0.1 mM LA + 0.1 mM ARA | | | |
|---|---|---|---|---|
| | ALA output (mg/g) | ALA conversion (100%) | EPA output (mg/g) | EPA conversion (100%) |
| oPpFADS17-3 | 0.6 ± 0.1 | 6.6 ± 0.6 | 3.8 ± 0.1 | 51.5 ± 0.8 |
| oAiFADS17-3 | 0.5 ± 0.1 | 4.1 ± 1.2 | 3.4 ± 0.3 | 37.3 ± 0.7 |
| oPaFADS171 | 0.4 ± 0.1 | 3.6 ± 1.0 | 3.3 ± 0.1 | 47.0 ± 0.9 |
| Ctrl | 0 ± 0 | 0 ± 0 | 0 ± 0 | 0 ± 0 |

The analysis showed that the conversion of the recombinant transformant INVSc 1-oPpFADS17-3 and INVSc 1-oAiFADS17-3 and INVSc 1-oPaFADS17-1 to the 20C substrate is significantly higher than the 18C substrate, and of which the conversion efficiency for ARA was particularly obvious. The conversion rate of INVSc 1-oPpFADS17-3 to ARA was the highest, and was the same as that of positive control INVSc 1-oPaFADS17-1, and the yield was higher than that of positive control. In addition, the conversion rate of INVSc 1-oPpFADS17-3 to ω-6 PUFAs outside ARA was about two times that of the positive control, indicating that the efficiency of ω-3 PUFAs synthesis of the recombinant bacteria of the present invention was significantly higher than that of positive control.

In order to prove that the catalytic activity of ω-3 fatty acid desaturase at normal temperature and lower temperature is higher, 0.2 mM LA, GLA, DGLA, ARA were added respectively and 0.1 mM LA and 0.1 mM ARA were added at the same time to the inducible medium, at 12° C. The result is as shown in table 4.

TABLE 4

Catalytic efficiency of different ω-3 desaturation *Saccharomyces cerevisiae* recombinant transformant on different substrates at 12° C.

| recombinant transformant (INVSc 1-) | 0.2 mM LA | | 0.2 mM GLA | | 0.2 mM DGLA | | 0.2 mM ARA | |
|---|---|---|---|---|---|---|---|---|
| | ALA output (mg/g) | ALA conversion (100%) | SDA output (mg/g) | SDA conversion (100%) | ETA output (mg/g) | ETA conversion (100%) | EPA output (mg/g) | EPA conversion (100%) |
| oPpFADS17-3 | 1.3 ± 0.1 | 4.7 ± 0.2 | 0.7 ± 0.1 | 3.1 ± 0.7 | 3.2 ± 0.3 | 17.7 ± 1.1 | 3.9 ± 0.3 | 30.9 ± 2.8 |
| oAiFADS17-3 | 0.5 ± 0.1 | 1.9 ± 0.2 | 0.2 ± 0.1 | 1.2 ± 0.4 | 1.4 ± 0.2 | 8.4 ± 0.4 | 1.6 ± 0.2 | 15.0 ± 0.9 |
| oPaFADS171 | 0.8 ± 0.1 | 3.5 ± 0.5 | 0.4 ± 0.1 | 2.1 ± 0.3 | 2.0 ± 0.1 | 12.4 ± 1.4 | 3.4 ± 0.1 | 26.0 ± 1.4 |
| Ctrl | 0 ± 0 | 0 ± 0 | 0 ± 0 | 0 ± 0 | 0 ± 0 | 0 ± 0 | 0 ± 0 | 0 ± 0 |

| recombinant transformant (INVSc 1-) | 0.1 mM LA + 0.1 mM ARA | | | |
|---|---|---|---|---|
| | ALA output (mg/g) | ALA conversion (100%) | EPA output (mg/g) | EPA conversion (100%) |
| oPpFADS17-3 | 0.8 ± 0.1 | 5.9 ± 0.7 | 3.9 ± 0.1 | 33.2 ± 1.6 |
| oAiFADS17-3 | 0.5 ± 0.1 | 4.1 ± 1.2 | 3.4 ± 0.3 | 37.3 ± 0.7 |
| oPaFADS171 | 0.2 ± 0.1 | 2.1 ± 0.4 | 2.3 ± 0.3 | 25.9 ± 0.9 |
| Ctrl | 0 ± 0 | 0 ± 0 | 0 ± 0 | 0 ± 0 |

The results of fatty acid determination in Table 4 showed that the conversion rates of different recombinant bacteria were lower at lower temperature. However, in the present invention, the recombinant *Saccharomyces cerevisiae* that can express ω-3 fatty acid desaturase from *Phytophthora parasitica* had significantly higher EPA conversion and EPA output than those of the recombinant *Saccharomyces cerevisiae* that can express ω-3 fatty acid desaturase from *Aphanomyces invadans* at a lower temperature. They were also better than those of the recombinant *Saccharomyces cerevisiae* that can express ω-3 fatty acid desaturase from *Pythium aphanidermatum.*

2. Recombinant *M. alpina* Expressing ω-3 Fatty Acid Desaturase from *Phytophthora parasitica*

Example 10: Constructing Expression Vector pBIG2-ura5s-oPpFADS17

The ω-3 fatty acid desaturase from *Phytophthora* parasitism was optimized according to the characteristics of *M. alpina*, and the optimized gene sequence oPpFADS17m (as shown by SEQ ID No.5) was ligated with pUC57 carrier to obtain pUC57-oPpFADS17 (PUC57-oPpFADS17 in CN 201610184669.X).

At 37° C., the plasmids pUC57-oPpFADS17 and vector pBIG2-ura5s-ITs fragments were overnight enzyme digested by the restriction endonuclease Hind III. The Hind III enzyme digestion system (100 μL) was: 2 μL Hind III-HF, 30 μL plasmid or vector, 10 μL Cutsmart Buffer, 58 μL deionized water, incubated at 37° C. for 12 h.

In which, vector pBIG2-ura5s-Its was directly obtained according to Chinese Patent Application No. CN201310524221.4.

The expression unit HPH was obtained from pD4 plasmid by PCR. The expression unit HPH was enzyme digested with restriction endonuclease EcoR I and Xba I and inserted into the MCS of pET28a(+) which was enzyme digested by EcoR I and Xba I, to obtain the plasmidpET28a-HPHs. The ura5 (orotate phosphoribosyl transferase, OPRTase) gene was obtained from *M. alpina* by PCR. The ura5 gene was enzyme digested by restriction endonuclease BspH I and BamH I, then the digested ura5 gene was inserted into the plasmid pET28a-HPHs which was enzyme digested by Nco I and BamH I, to replace the gene hpt and construct the plasmid pET28a-ura5s. The expression unit ura5s was obtained by digestion of plasmid pET28a-ura5s with the restriction enzyme EcoR I and Xba I. The expression unit ura5s was used to replace the expression unit HPH in plasmid pBIG2RHPH2, and plasmid transformation plasmid pBIG2-ura5s was further constructed. Furthermore, based on plasmid pBIG2-ura5s and plasmid pET28a-HPHs, a general carrier for genetic manipulation of *M. alpina* was constructed. A non-coding intron DNA fragment IT was obtained from the genome of *M. alpina* by PCR. The restriction endonuclease NcoI and BamHI were used to digest the IT gene fragment and plasmid pET28a-HPHs respectively, and hpt gene of the plasmid pET28a-HPHs was replaced by the IT fragment through the legation reaction to obtain the plasmid pET28a-ITs. ITs expression unit was obtained by double digesting the plasmid pET28a-ITs with restriction endonuclease Spe I and Xba I. The ITs expression unit was inserted into the plasmid pBIG2-ura5s which was digested with Xba I, a general carrier pBIG2-ura5s-ITs for genetic manipulation of *M. alpina* was constructed.

The digestion products were recovered and further digested with restriction endonuclease Xho I, and then the aimed gene (ω-3 fatty acid desaturase gene fragment oPpFADS17m from *Phytophthora parasitica*, optimized for *M. alpina*, oPpFADS17 in CN 201610184669X) and vector pBIG2-ura5s-ITs fragments were recovered by cutting gel. The enzyme digestion system (100 μL) was: 2 μL Xho I, 30 μL plasmid or vector pBIG2-ura5s-ITs fragment, 10 μL cutsmart Buffer, 58 μL deionized water, digested at 37° C. water bath for 12 h.

In which, the enzyme buffer Cutsmart buffer: 50 mM acetic acid, 20 mM Tris-acetic acid, 10 M magnesium acetate, 100 μg/mL bovine serum albumin, pH 7.9.

Then, the T4 ligase was used to ligate the ω-3 fatty acid desaturase gene fragment oPpFADS17m with the vector pBIG2-ura5s-ITs, at 4° C. for 12 h, to obtain the recombinant expression vector pBIG2-ura5s-oPpFADS17. The ligation system (10 μL) is: 2 μL target gene fragments after digestion, 3 μL carrier fragments after digestion, 1 μL ligase buffer, 1 μL T4 ligase, 3 μL sterile water, ligating at 4° C. for 12 h.

The method for transforming *E. coli* TOP10 competent cells with the ligation products is as follows:

(1) In the aseptic state, 100 μL of the competent cells were taken, and 1-2 μL ligation product were added and the mixture was blown and mixed well.

(2) The mixed competent cells were moved into the pre-cooled electric rotating cup to avoid bubbles.

(3) The electric rotating cup was put into Bio-Rad electric rotary instrument and adjusted into a propriate preset program position. The electrical transformation was carried out at the voltage condition of 1.8 kV.

(4) 1 mL SOC resuscitation medium was added into the transformed competent cells, mixed, and then transferred into a 1.5 mL centrifugation tube and incubated at 37° C. and 150 rpm for 1 h.

(5) A LB solid medium plate containing 100 μg/mL ampicomycin was coated with 200 μL of the obtained product, and reversed and incubated at 37° C. overnight.

The positive transformants were picked up, the plasmids were extracted, the results of sequencing proved that the ligation was successful and binary expression vector pBIG2-ura5s-oPpFADS17 was obtained.

The binary expression vector pBIG2-ura5s-oPpFADS17 was used to transform 15 *Agrobacterium tumefaciens* by means of transformation of *E. coli* TOP10. *Agrobacterium tumefaciens* C58C1 containing plasmid pBIG2-ura5s-oPpFADS17 was obtained.

Example 11: ATMT of *M. alpina*

The transformation was optimized according to the method referred to the open accessed articles, the detailed steps are as follows:

(1) *A. tumefaciens* C58C1 harboring pBIG2-ura5s-oPpFADS17 preserved at the temperature of −80° C. was put on the YEP solid plate (containing 100 lag/mL rifampicin and 100 μg/mL kanamycin), reversed incubating at the temperature of 28° C. for 48 h in the dark.

(2) A single clone was transferred to a 20 mL liquid YEP medium (containing 100 μg/mL rifampicin and 100 μg/mL kanamycin) and cultured at 28° C. and 200 rpm for 24-48 h in the dark.

(3) Bacteria was collected by centrifuging at 4000×g for 5 min. the suspension was removed, pellet was suspended by 5 mL IM medium, followed by a centrifugation at 4000×g for 5 min. After removing the suspension, 2 mL of IM medium were added to suspend the bacterium.

(4) The concentration of the bacterium suspension to $OD_{600}$=0.3, followed by a dark cultivation at 28° C. and shaking at 200 rpm to $OD_{600}$=1.0;

(5) 500 μL sterilized physiological saline was used to wash *M. alpina* uracil auxotrophic strain CCFM501 (i.e. uracil auxotrophic strain MAU1 disclosed in CN 201310347934.8) with GY-U slant culture for more than one month. Spores were collected and counted with a haemacytometer to adjust the concentration of spores to $10^7$/100 μL.

(6) 100 μL *Agrobacterium tumefaciens* was mixed with 100 μL spores and evenly coated on the IM solid medium with cellophane. Incubated at 23° C. for 36-48 h in the dark.

(7) The cellophane was transferred to the SC plate (SC-CS) containing 100 μg/mL of the spectinomycin and 100 μg/mL cefotaxime antibiotics. The culture was carried out at 18° C. for 12 h and then transferred to 25° C.

(8) The growth of the colony on the SC-CS plate was continuously observed. If the colonies were grown out, the outer edge was excavated in time with the sharp tweezers and inoculated on the SC-CS plate, and continued to be placed in the 25° C. incubator.

(9) After the transformants on the SC-CS plate grew, the mycelia were transferred to the SC-CS plate, and screened repeatedly for 3 times to eliminate the negative transformants.

(10) The bacterial colony which grew after three time's screening was inoculated to the GY plate, cultured at 28° C. to produce a large number of spores and stored at 4° C.

Example 12: Screening and Identifying of *M. alpina* for Overexpressing oPpFADS17m (1) 3 mL physiological saline was used to wash GY's surface. Liquid was collected in a sterile 1.5 mL centrifuge tube and then filter with 25 μm membrane.

(2) The spore concentration was counted with a haemacytometer and three kinds of spores concentration gradient were adjusted to $10^8$/100 μL, $10^6$/100 μL and $10^4$/100 μL each, and each with 200 μL coated on the GY-CS tablet containing 100 μg/mL of cefotaxime and 100 μg/mL cefotaxime, then cultured at 25° C. for 2-3 days in the dark;

(3) The growing fungal mycelium was picked by sterile forceps and placed on a SC-CS plate, and then incubated at 25° C. for 2-3 days;

(4) The growth of *M. alpina* on the plate was observed. The mycelium grown on the SC-CS plate were picked and inoculated onto the GY slope;

(5) The *M. alpine* strain spores in the above step 4) were cultured on the GY medium for 3 times;

(6) The strains with hereditary stability were identified as recombinant *M. alpina* for heterologous expressing oPpFADS17m and kept on the GY slope;

(7) The right genomic DNA of the recombinant *M. alpine* were extracted and identified, and PCR verification was performed with a pair of primers specifically binding to promoters and terminators:

```
P1 (sense):
CACACACAAACCTCTCTCCCACT

P2 (antisense):
CAAATGAACGTATCTTATCGAGATCC;
```

The results of agarose gel electrophoresis analysis of recombinant strains were shown in FIG. 6. M was marker; swim Lane 1 was negative control; swimming lane 2-6 were 1-5 MA-oPpFADS17 recombinant strain. The results showed that five positive transformants could amplify two product bands of 818 bp and 1086 bp, respectively. The electrophoresis results showed that all the 1-5 transformants were positive transformants, in which binary expression vectors successfully integrated into the genome of *M. alpina*.

(8) The obtained recombinant strains were kept on GY slope respectively.

Example 13: Extraction of Total RNA from Positive Transformants MA-oPpFADS17

(1) Appropriate amount of bacteria frozen in liquid nitrogen was removed, and liquid nitrogen was added to the precooled aseptic and enzyme-free mortar and ground well (2) 1 mL TRIzol (purchased from Invitrogen, Carlsbad, Calif., USA) were added and continued to grind to powder and then put at the room temperature to dissolve.

(3) An enzyme free gun head was used to extract 1 mL of the above liquid in an enzyme free centrifuge tube and mixed with 200 μL of trichloromethane.

(4) Centrifuged at 13200×g and at 4° C. for 15 min, and the supernatant was sucked in a new enzyme free centrifuge tube.

(5) Mixed with 200 μL trichloromethane, and centrifuged at 13200×g and 4° C. for 15 min, and the supernatant was sucked in a new enzyme free centrifuge tube.

(6) Equal volume of isopropanol was added and rest for 15 min, then centrifuged at 13200×g and 4° C. for 15 min. The supernatant was removed and then dried at room temperature.

(7) 1 mL 70 vol % ethanol was added, then centrifuged at 13200×g and 4° C. for 15 min. An enzyme free gun head was used to suck out ethanol and put to dry at room temperature.

(8) 50 μL enzyme free water was added to dissolve RNA and stored at −80° C.

(9) Determination of concentration: 1 μL RNA was taken out and measured its concentration with NaNodrop 2000.

(10) Detecting of the integrity of RNA by denaturing gel electrophoresis: The integrity of RNA was observed by electrophoresis of 1 μg RNA in 1.2 wt % denaturing gel.

(11) 1 μg total RNA was taken as the template, and the cDNA of the recombinant strain was obtained according to the operation of PrimeScript RT reagent kit (TaKaRa, Otsu, Shiga, Japan).

Example 14: RT-qPCR Detection of Transcriptional Level of Positive Transformant MA-oPpFADS17

Primers were designed according oPpFADS17 sequence and internal standard 18SrRNA sequence:

```
q-oPpFADS17m F:
TCTTCCCCACCCTCACCG

(q-oPpFADS17 F in CN 201610184669.X)

q-oPpFADS17m R:
CAAGCCACGAGCGTAGTTCA

(q-oPpFADS17 R in CN 201610184669.X)

18SRTF:
CGTACTACCGATTGAATGGCTTAG

18SRTR:
CCTACGGAAACCTTGTTACGACT
```

0.5-1 μg cDNA was taken as template, and RT-qPCR reaction was performed according to the instructions of iTaq Universal SYBR Green Supermix by using Bio-Rad CFX Connect™ system. The reaction system is: 8 μL enzyme-free water, 10 μL iTaq Universal SYBR Green Supermix, 0.5 μL q-oPpFADS17m F, 0.5 μL q-oPpFADS17-m R, 1 μL template, with a total volume of 20 μL. The PCR cycle is set at 50° C. for 2 min, 95° C. for 10 min, 95° C. for 15 s, 60° C. for 30 s, 30 cycles. 18S rRNA of *M. Alpina* was taken as internal reference gene, each transformants was taken three parallel lines.

Results as shown in FIG. 7, ω-3 fatty acid desaturase gene (oPpFADS17m) in the wild type of *M. alpina* as a control was not transcribed, and the transcription level of ω-3 fatty acid desaturase gene (oPpFADS17m) of 5 genetically engineered stains were significantly increased. This suggests that the *Agrobacterium tumefaciens* mediated method can be used to transcribe and express exogenous ω-3 fatty acid desaturase gene, which is optimized for *M. alpina*, oPpFADS17m from *Phytophthora parasitica*), in *M. alpina.*

Example 15: Extraction of Fatty Acid from Positive Transformant (1) The *M. alpina* prototrophic strain and *M. alpina* strains for overexpressing oPpFADS17m which were screened in Example 3 were inoculated in Broth medium, incubated at the temperature of 28° C. at 200 rpm for 7 d.

(2) The bacteria were collected, vacuum freeze-dried to constant weight, weighed and calculated biomass.

(3) The bacteria were grinded into powder, and 50 mg was weighed, and 2 mL 4 M hydrochloric acid was added.

(4) Water bath at 80° C. for 1 h, then at −80° C. for 15 min. Repeat once. Then water bath at 80° C. for 1 h.

(5) Cooled down to room temperature, then 1 mL methanol were added and mixed well.

(6) 1 mL chloroform were added and shaken for 10 min, followed by centrifuge at 3000×g for 3 min. Chloroform were collected.

(7) Repeat step (6) twice.

(8) Chloroform (3 mL) were combined. 1 mL saturated NaCl solution were added and mixed well, and then centrifuged at 3000×g for 3 min. Chloroform layer were collected into a new tube. 1 mL chloroform were added in the residual liquid, followed by centrifugation at 3000×g for 3 min. All the chloroform (4 mL) were combined.

(9) After dried by nitrogen blow, 1 mL ether were added and transferred to a clean and weighed tube, followed by drying by nitrogen blow.

Example 16: Detection of Fatty Acid from Positive Transformant

The method for detecting the composition and content of fatty acid is as follows:

(1) 100 μL 2.02 mg/mL internal standard C15:0 and 1 mL 10 wt % methanolic hydrochloride were added into the above crude fat. At 60° C. water bath for 3 h, the mixture were vibrated for 1 min every 30 min.

(2) After cooling to room temperature, 1 mL n-hexane and 1 mL saturated sodium chloride solution were added, vibrated and mixed, centrifuged at 3000×g for 3 min. The hexane layer was sucked out and 1 mL hexane were added and vibrated and mixed, centrifuged at 3000×g for 3 min. N-hexane were sucked out and merged.

(3) After nitrogen drying at 37° C., 1 mL of n-hexane was added and mixed, then transferred into the gas bottle to obtain fatty acid methyl ester solution.

(4) Fatty acid methyl esters were analyzed by GC-2010 (Shimadzu Co., Japan) and DB-Waxetr (30 m×0.32 mm, 0.22 μm) as the chromatographic column. The detection was performed by hydrogen flame ionization detector, under the temperature of the vaporization chamber and detector at 240° C. and 260° C. respectively. 1 μL samples were injected by distributary injection, the split ratio was 10:1, and the carrier gas was helium. Temperature programmed: the initial temperature was 120° C. for 3 min, 5 C/min to 190° C., then 4° C./min to 2200° C. for 20 min, and at last 5° C./min to 220° C., and for 17 min. Qualitative and quantitative analysis of fatty acids' composition in samples was carried out by comparison with quality of commercial fatty acid methyl ester standard product (37 kinds of fatty acid methyl esters mixed standard, Supelco, USA) and the added internal standard C15:0.

Table 5 is the comparison of fatty acid yield between the wild (protrophic type) *M. alpina* and five *M. alpina* strains expressing oPpFADS17m gene from *Phytophthora parasitica*. The table 6 is the comparison of fatty acid composition between the wild *M. alpina* and the five *M. alpina* strains expressing oPpFADS17m gene from *Phytophthora parasitica.*

The results of table 5 and table 6 showed that there was no significant difference in biomass between five genetic engineering strains and wild-type strains, but the composition of fatty acid changed significantly. Among the five recombinant strains, the yield of AA (C20:4) was reduced in varying degrees than in the wild type, and a large number of EPA (C20:5) were produced, and the reduction of output of AA and increase in production of EPA had obvious regularity, while the yield of the other fatty acids (C16:0, C18:0, C18:1, C18:2, C18:3) had no significant changes, which indicated that all five strains of recombinant strains can catalyze AA to EPA in varying degrees. In which, MA-oPpFADS17-4 showed excellent EPA production, the output of EPA reached 1197.3 mg/L, accounting for 31.5% of total fatty acid (TFA), and its AA yield was only 326.8 mg/L, indicating that most AA could be converted to EPA, and the conversion rate of AA was 77.6% (conversion rate=EPA/(AA+EPA)*100%). In addition, the absolute value of TFA also increased to a certain extent.

In addition, the other four recombinant strains (MA-oPpFADS17-1, 2, 3 and 5) also showed different levels of increase in EPA production, which was significantly different from the wild-type strains. This indicates that the ω-3 fatty acid desaturase gene oPpFADS17m from *Phytophthora parasitica* can be successfully expressed in *M. alpina*, and the recombinant bacteria obtained according to the construction method of the present invention can convert AA into EPA and have considerable conversion rate. Among them, MA-oPpFADS17-4 has the most obvious effect, compared with other MA-oPpFADS17 transformants, has an unexpected improvement, which is also significantly higher than the other existing techniques.

TABLE 5

| Comparison of fatty acid production between wild type strain and five genetic engineering strains of *M. alpina* | | | | |
|---|---|---|---|---|
| Strains | Biomass (g/L) | AA(mg/L) | EPA(mg/L) | TFA(g/L) |
| *M. alpina* | 11.1 ± 0.2 | 1264.8 ± 33.6 | 0.0 ± 0.0 | 3.1 ± 0.1 |
| MA-oPpFADS17-1 | 11.2 ± 0.3 | 1174.8 ± 19.7 | 105.6 ± 13.7 | 3.3 ± 0.1 |
| MA-oPpFADS17-2 | 10.9 ± 0.1 | 1094.4 ± 26.1 | 195.2 ± 14.5 | 3.2 ± 0.1 |
| MA-oPpFADS17-3 | 11.1 ± 0.3 | 682.0 ± 17.3 | 558.2 ± 31.7 | 3.1 ± 0.1 |
| MA-oPpFADS17-4 | 11.6 ± 0.1 | 326.8 ± 11.4 | 1197.3 ± 21.8 | 3.8 ± 0.1 |
| MA-oPpFADS17-5 | 11.1 ± 0.1 | 682.5 ± 17.7 | 819.4 ± 13.4 | 3.5 ± 0.1 |

TABLE 6

| Comparison of fatty acid composition between wild type strain and five genetic engineering strains of *M. alpina* | | | | | | | |
|---|---|---|---|---|---|---|---|
| | Content of various fatty acids (% TFA) | | | | | | |
| Strains | C16:0 | C18:0 | C18:1 | C18:2 | C18:3 (n-6) | C20:4 (n-6) | C20:5 |
| *M. alpina* | 11.3 ± 0.4 | 10.4 ± 0.3 | 17.2 ± 1.4 | 8.8 ± 0.1 | 5.2 ± 0.1 | 40.8 ± 3.1 | 0 ± 0 |
| MA-oPpFADS17-1 | 12.6 ± 0.4 | 11.4 ± 0.4 | 16.7 ± 0.5 | 9.1 ± 0.1 | 5.4 ± 0.1 | 35.6 ± 2.3 | 3.2 ± 0.1 |
| MA-oPpFADS17-2 | 11.6 ± 0.7 | 11.4 ± 0.3 | 15.9 ± 0.4 | 9.2 ± 0.1 | 5.6 ± 0.1 | 34.2 ± 1.2 | 6.1 ± 0.1 |
| MA-oPpFADS17-3 | 12.9 ± 0.8 | 11.7 ± 0.6 | 16.2 ± 0.1 | 9.6 ± 0.3 | 5.1 ± 0.1 | 22.0 ± 1.1 | 18.0 ± 1.0 |
| MA-oPpFADS17-4 | 13.3 ± 0.4 | 10.4 ± 0.4 | 18.0 ± 0.9 | 10.5 ± 0.2 | 5.3 ± 0.1 | 8.6 ± 0.4 | 31.5 ± 2.7 |
| MA-oPpFADS17-5 | 11.5 ± 0.5 | 10.9 ± 0.4 | 16.3 ± 0.9 | 9.5 ± 0.1 | 5.2 ± 0.1 | 19.5 ± 2.0 | 23.4 ± 1.0 |

The results show that the recombinant *M. alpina* overexpressing ω-3 fatty acid desaturase gene (oPpFADS17m) from *Phytophthora parasitica*, obtained according to the method of the present invention, have genetic stability for multiple passage. Furthermore, compared with the wild-type, there is no significant difference in the fatty acid analysis results for the products obtained by the normal temperature culture. The yield of EPA was improved, of which the EPA production of the strain MA-oPpFADS17-4 has reached 31.5% of the total fatty acid, compared with the wild type, the yield of EPA was significantly higher than that of the other recombinant strains obtained by the same method. It was also significantly higher than the production of EPA by normal temperature culture of other known recombinant *M. alpina* overexpressing ω-3 fatty acid desaturase gene. The genetic engineering strains constructed by this method and their construction methods laid a theoretical and applied foundation for subsequent industrialization.

To sum up, ω-3 fatty acid desaturase obtained according to the present invention can catalyze both 18C and 20C polyunsaturated fatty acids, but prefer converting 20C ARA to EPA, and the conversion efficiency at normal temperature is obviously higher. Furthermore, the efficiency of the synthesis of ω-3 PUFAs is further superior to the existing technology. Using this gene to construct genetic engineering strains laid a foundation for subsequent industrial production of EPA and DHA.

It should be appreciated that the foregoing is only preferable embodiments of the invention and is not for use in limiting the invention. Any modification, equivalent substitution, and improvement without departing from the spirit and principle of this invention should be covered in the protection scope of the invention.

What is claimed is:

1. A recombinant *Mortierella alpine* MA-oPpFADS17-4 strain, overexpressing ω-3 fatty acid desaturase from *Phytophthora parasitica*, was preserved in China General Microbiological Culture Collection Center (CGMCC) since Jan. 18, 2016, with the accession number CGMCC No. 11820, the address of CGMCC being No. 3, Courtyard 1, Beichen West Road, Chaoyang District, Beijing, the Institute of Microbiology, Chinese Academy of Science.

2. The recombinant *Mortierella alpine* according to claim 1, characterized in that said ω-3 fatty acid desaturase oPpFADS17m gene from *Phytophthora parasitica* is optimized according to the codon usage bias of *Mortierella alpine*, and has the nucleic sequence shown as SEQ ID NO: 5.

3. The recombinant *Mortierella alpine* according to claim 1, characterized in that the strain is constructed by using the recombinant plasmid pBIG2-ura5s-oPpFADS17 containing ω-3 fatty acid desaturase oPpFADS17m gene to convert *A. tumefaciens* and then to the *M. alpina* uracil auxotrophic strain with *A. tumefaciens* containing transformation plasmids pBIG2-ura5s-oPpFADS17.

4. The recombinant *M. alpine* according to claim 3, characterized in that *M. alpina* uracil auxotrophic strain is a strain that can inactivate the ura5 encoding orotate phosphoribosyltransferase (OPRTase) in *M. alpina* ATCC32222.

5. A method for constructing the recombinant *M. alpine* according to claim 1, comprising the following steps:

a) artificially synthesizing the codon optimized ω-3 fatty acid desaturase gene oPpFADS17m from *Phytophthora parasitica*, according to the condon usage bias of *M. alpina* where the codon optimized ω-3 fatty acid desaturase is shown as SEQ ID NO: 5;

b) constructing the recombinant plasmid pBIG2-ura5s-oPpFADS17;

c) transforming the obtained recombinant plasmid pBIG2-ura5s-oPpFADS17 into *A. tumefaciens;* d) transforming *M. alpina* uracil auxotrophic strain with *A. tumefaciens* containing the recombinant plasmid pBIG2-ura5s-oPpFADSU;

e) screening and identifying the transformed strains special for an EPA producing recombinant *M. alpina* MA-oPpFADS17-A that overexpresses ω-3 fatty acid desaturase oPpFADS17m.

6. The method according to claim 5, characterized in that in the said step c), *A. tumefaciens* is *A. tumefaciens* C58C1.

7. The method according to claim 5, characterized in that, in the said step d), *M. alpina* uracil auxotrophic strain is *M. alpina* MAU1, which was preserved in China General Microbiological Culture Collection Center (CGMCC) since Nov. 1, 2013, with the accession number CGMCC No. 8414.

8. The method for constructing the recombinant *M. alpine* strain according to claim 4, characterized in that in the said step e), the method for screening and identifying the transformed strains comprises the following steps:

1) scouring the surface of GY medium with 3 mL saline, and collecting liquid in a sterile 1.5 mL centrifuge tube and then filtering with 25 µm filter membrane;

2) counting the spore concentration with a haemacytometer and adjusting the concentration to $10^8$/100 µL, $10^6$/100 µL and $10^4$/100 µL each, and each with 200 µL coating on the GY-CS tablet containing 100 µg/mL of cefotaxime and 100 µg/mL cefotaxime, then culturing at 25° C. for 2-3 days in the dark;

3) picking the fungal mycelium by sterile forceps and placing them on a SC-CS plate containing 100 µg/mL of the mycin and 100 µg/mL cefotaxime, and then culturing at 25° C. for 2-3 days in the dark;

4) observing the growth of *M. alpina* on the plate, and picking the mycelium on the SC-CS plate onto the GY slope;

5) culturing the *M. alpine* strain spores in the above step 4) on the GY medium for 3 times;

6) identifying the strains with hereditary stability as recombinant *M. alpina* with overexpression of ω-3 fatty acid desaturase oPpFADS17m, and keeping it on the GY slope;

7) extracting the genomic DNA of the recombinant *M. alpine*, and designing a pair of primers with specific promoters and terminators for PCR verification;

```
P1 (sense):
CACACACAAACCTCTCTCCCACT

P2 (antisense):
CAAATGAACGTATCTTATCGAGATCC;
```

8) keeping the recombinant *M. alpina* on the GY slope.

9. The use of the recombinant *M. alpine* strain MA-oPpFADS17-4 according to claim 1 or those obtained according to the method according to claim 5 in the production of fatty acid.

10. The use of the recombinant *M. alpine* strain MA-oPpFADS17-4 according to claim 9, the fatty acid is EPA.

* * * * *